(12) United States Patent
Bouillé et al.

(10) Patent No.: US 10,273,462 B2
(45) Date of Patent: Apr. 30, 2019

(54) VIRUS-BASED VECTOR COMPOSITIONS USEFUL FOR TRANSDUCING EUKARYOTIC CELLS

(75) Inventors: Pascale Bouillé, Escalquens (FR); Hélène Vergnault, Toulouse (FR); Régis Gayon, Ramonville Saint Agne (FR); Yohann Moal, Toulouse (FR)

(73) Assignee: Vectalys SAS, Toulouse (FR)

(*) Notice: Subject to any disclaimer, the term of this patent is extended or adjusted under 35 U.S.C. 154(b) by 49 days.

(21) Appl. No.: 13/558,981

(22) Filed: Jul. 26, 2012

(65) Prior Publication Data

US 2013/0029379 A1   Jan. 31, 2013

Related U.S. Application Data

(60) Provisional application No. 61/512,289, filed on Jul. 27, 2011.

(51) Int. Cl.
C12N 7/02 (2006.01)

(52) U.S. Cl.
CPC ...... *C12N 7/02* (2013.01); *C12N 2740/15051* (2013.01)

(58) Field of Classification Search
CPC ....................................................... C12N 7/02
See application file for complete search history.

(56) References Cited

U.S. PATENT DOCUMENTS

2009/0060950 A1* 3/2009 Kistner et al. ............. 424/209.1

OTHER PUBLICATIONS

Sena-Esteves et al. (1999, J. Virology, vol. 73(12), pp. 10426-10439).*
Segura et al. (2007, Biotechnology and Bioengineering, vol. 98(4), pp. 789-799).*
Geraerts et al. (2005, J. Gene Medicine, vol. 7, pp. 1299-1310).*
Cabasso et al. (1976, J. Applied Polymer Science, vol. 20, pp. 2377-2394).*
Zimmermann et al. (2011, BMC Biotechnology, vol. 11, pp. 1-12).*
MP Biomedicals product printout for Heparin-Agarose, 3 pages.*
Merten et al. (ePub Nov. 2010, Human Gene Therapy, vol. 22, pp. 343-356). (Year: 2010).*
Millipore Fast-Trap Product Brochure 2-pages (Year: 2008).*
Sena-Esteves et al. (1999, J. Virology, vol. 73(12), pp. 10426-10439) (Year: 1999).*
Segura et al. (2007, Biotechnology and Bioengineering, vol. 98(4), pp. 789-799) (Year: 2007).*
Geraerts et al. (2005, J. Gene Medicine, vol. 7, pp. 1299-1310) (Year: 2005).*
Zimmermann et al. (2011, BMC Biotechnology, vol. 11, pp. 1-12) (Year: 2011).*
Cabasso et al. (1976, J. Applied Polymer Science, vol. 20, pp. 2377-2394) (Year: 1976).*
Turner et al. (2009, Molecular Therapy, vol. 17(2), pp. 360-368) (Year: 2009).*
Millipore Fast-Trap System (2008). (Year: 2008).*
Sastry et al. (2004, Human Gene Therapy, vol. 15, pp. 221-226) (Year: 2004).*
Aloia, R. et al., "Lipid composition and fluidity of the human immunodeficiency virus envelope and host cell plasma membranes", Proc. Natl. Acad. Sci. USA (1993), vol. 90:11, pp. 5181-5185.
Andreadis, S.T. et al., "Large-scale processing of recombinant retroviruses for gene therapy", Biotechnol. Prog. (1999), vol. 15, pp. 1-11.
Ansorge, S., et al., "Recent Progress in Lentiviral Vector Mass Production" Biochemical Engineering Journal (2010), vol. 48, pp. 362-377.
Baekelandt, V. et al., "Optimized lentiviral vector production and purification procedure prevents immune response after transduction of mouse brain", Gene Therapy (2003), vol. 10, pp. 1933-1940.
Brunner, D. et al., Serum-free Cell Culture: the Serum-free Media Interactive Online Database, Altex 27, vol. 27:1, pp. 53-62.
Clapham, P. et al., "Pseudotypes of human T-cell leukemia virus types 1 and 2: Neutralization by patients' sera", PNAS USA (1984), vol. 81, pp. 2886-2889.
Coffin, J.M. et al., (eds.) Retroviruses. Cold Spring Harbor Laboratory Press (1997), Table of Contents only.
Cooper A.R. et al., "Highly efficient large-scale lentiviral vector concentration by tandem tangential flow filtration", Jour. Vir. Methods, vol. 177:1, pp. 1-9 (2011).
Corodinha, A.S. et al., "Effect of medium sugar source on the production of retroviral vectors for gene therapy", Biotech. Bioeng. (2006), vol. 94:2, pp. 24-36.
Geraerts, M., et al., "Upscaling of Lentiviral Vector Production by Tangential Flow Filtration" The Journal of Gene Medicine (2005); vol. 7, pp. 1299-1310.
Grzenia D.L. et al., "Tangential flow filtration for virus purification", J. Membrane Sci. (2008), vol. 321, pp. 373-380.
Le Doux, J. M. et al., "Kinetics of retrovirus production and decay", Biotech. Bioeng. (1999), vol. 63:6, pp. 654-662.
Logan, A. C., et al., "Factors Influencing the Titer and Infectivity of Lentiviral Vectors", Human Gene Therapy (2004), vol. 15, pp. 976-988.

(Continued)

*Primary Examiner* — Thaian N Ton
*Assistant Examiner* — David A. Montanari
(74) *Attorney, Agent, or Firm* — Buchanan Ingersoll & Rooney PC

(57) ABSTRACT

The present invention provides viral vector compositions of high titer and purity, as well as methods for production of said compositions. The methods of the invention incorporate multiple features, such as production of viral vector particles in serum free media and multiple harvesting steps following transduction of the producer cell which provides for enhanced production of said viral vectors. The viral vector compositions of the invention, by virtue of their high titer and purity, minimize the deleterious phenotypic changes that typically occur following transduction of target cells, such as loss of a sub-populations of transduced cells, and effects on proliferation, differentiation, reprogramming or functionality of transduced cells.

12 Claims, 21 Drawing Sheets

(56) References Cited

OTHER PUBLICATIONS

Manganini, M. et al., "A human immunodeficiency virus type 1 pol gene-derived sequence (cPPT/CTS) increases the efficiency of transduction of human nondividing monocytes and T lypmhocytes by lentiviral vectors", Human Gene Ther., (2002), vol. 13, pp. 1793-1807.
Merten, O.W. et al., "Large-scale manufacture and characterzation of a lentiviral vector produced for clinical ex vivo gene therapy application", Hum. Gene Ther., (2011), 45 pgs.
O'Keeffee, R.S. et al., "The affinity adsorptive recovery of an infectious herpes simplex virus vaccine", Biotechnol. Bioeng. (1999), vol. 62:5, pp. 537-545.
Ott, D.E. "Cellular proteins in HIV virons" Reviews in Meddical Virology (1997), vol. 7, pp. 167-180.
Reiser, J. "Production and concentration of pseudotyped HIV-1 based gene transfer vectors" Gene Therapy (2000), vol. 7, pp. 910-913.
Rimai, L. et al., "Electrophoretic mobilities of RNA tumor viruses. Studies by Doppler-shifted light scattering spectroscopy" Biochemistry (1975), vol. 14:21, pp. 4621-4627.
Rodrigues, T. et al., "Scaleable purification process for Gene Therapy retroviral vectors", J. Gene Medicine (2007), vol. 9, pp. 233-243.
Rodrigues, T. et al., "Purification of retroviral vectors for clinical application: Biological implications and technological challenges". J. Biotechnol. (2007), vol. 127, pp. 520-541.
Salmeen, I. et al., "Hydrodynamic diameters of RNA tumor viruses. Studies by laser beat frequency light scattering specyroscopy of avian myeloblastosis and Rauscher murine leukemia virses" Biochemistry (1975), vol. 14:1, pp. 134-141.
Segura, M. M., et al., "Production of Lentiviral Vectors by Large-Scale Transient Transfection of Suspension Cultures and Affinity Chromatography Purification" Biotechnol. Bioeng. (2007), vol. 98:4, pp. 789-799.
Selvaggi, T. A. et al, "Development of Antibodies to Fetal Calf Serum With Arthus-Like Reactions in Human Immunodeficiency Virus—Infected Patients Given Syngeneic Lymphocyte Infusions", Blood (1997) vol. 89:3, pp. 776-779.
Sena-Esteves, M. et al., "Optimized large-scale production of high titer lentivirus vector pseudotypes", Journal of Virological Methods (2004), vol. 122, pp. 131-139.
Slepushkin, V. et al, "Large scale purification of a lentiviral vector by size exclusion chromatography or mustang Q ion exchange capsule", BioProcessing Journal (2003), pp. 89-95.
Trubey, C.M. et al., "Quantification of HLA class II protein incorporated into human immunideficiency type 1 virions purified by anti-CD45 immunoaffinity depletion of microvesicles" J. Virol (2003). vol. 77:23, pp. 12699-12709.
Van Reis, R. et al., "Membrane separation in biotechnology" Curr. Opin. Biotech. (2001), vol. 12, pp. 208-211.
Verhoeyen, E. et al. "Surface-engineering of lentiviral vectors" J. Gene Med. (2004) vol. 6, pp. S83-S94.
Yamada, K. et al., "Lentivirus vector purification using anion exchange HPLC leads to improved gene transfer" Biotechniques (2003), vol. 34:5, pp. 1074-1080.
Yee, J.K. et al., "Generation of high-titer pseudotyped retroviral vectors with very broad host range" Methods Cell Biol. (1994), vol. 43, Part A, pp. 99-112.
Zufferey, R et al., "Woodchuck hepatitis virus posttranscriptional regulatory element enhances expression of transgenes delivered by retroviral vectors" Journal of Virology (1999), vol. 73:4, pp. 2886-2892.
International Search Report and Written Opinion from Counterpart International Patent Application No. PCT/IB2012/001807 filed Jul. 26, 2012.

\* cited by examiner

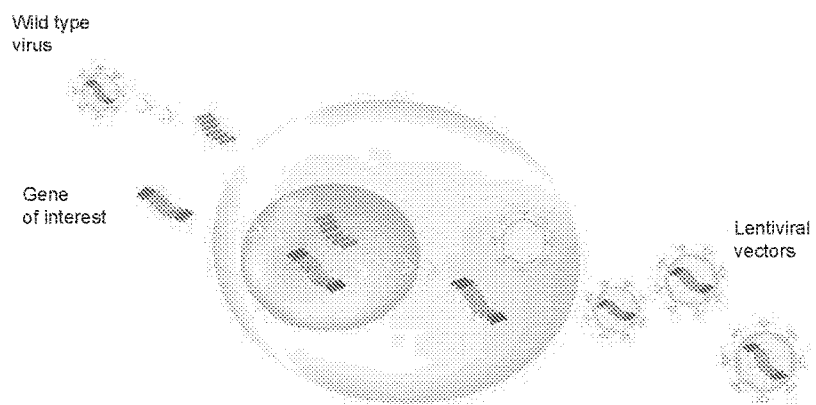
Figure 1: Vector production schema

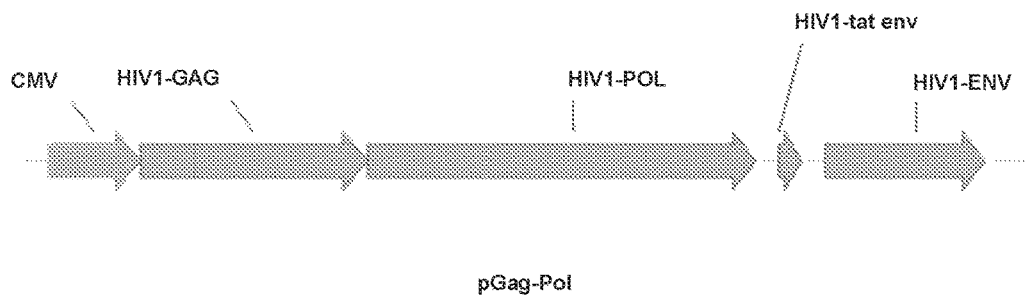
| FEATURES | Length (bp) | |
|---|---|---|
| promoter | 602 | /label=CMV |
| CDS | 1502 | /label=HIV1_gag |
| CDS | 2737 | /label=HIV1-pol |
| CDS | 1173 | /label=HIV1-env |
| protein_bind | 204 | /label=HIV1_RRE |
Figure 2A: Plasmid harboring gag and pol genes
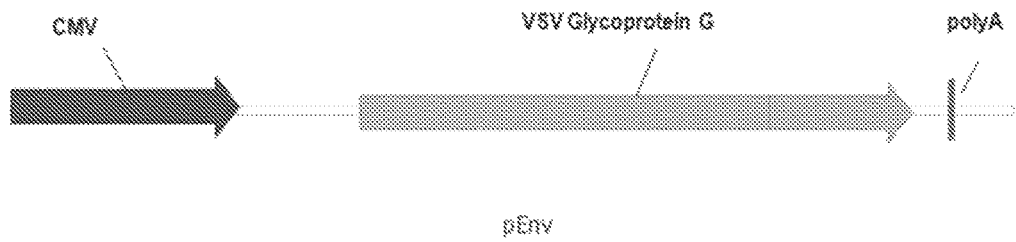
| FEATURES | Length (bp) | |
|---|---|---|
| Promoter | 677 | /label=CMV |
| CDS | 1642 | /label=VSV_glycoprotein\_G |
| polyA_signal | 768 | /label=HBB2 |
Figure 2B: Envelope expressing helper plasmid

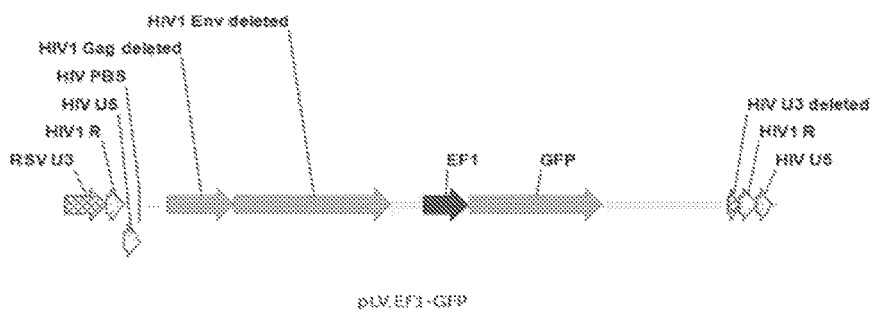
| FEATURES | Length (bp) | |
|---|---|---|
| repeat_region | 230 | /label=RSV_U3 |
| Feature | 119 | /label=packaging signal |
| CDS | 362 | /label=HIV1_gag |
| CDS | 856 | /label=HIV1tat-rev-env |
| Promoter | 236 | /label=EF1_promoter |
| CDS | 719 | /label=EGFP |
| Feature | 18 | /label=Primer Binding Site PBS |
| repeat_unit | 55 | /label=HIV_U3 deleted |
| repeat_unit | 95 | /label=HIV_R |
| repeat_unit | 85 | /label=HIV_U5 |
Figure 2C: Transgene expression plasmid

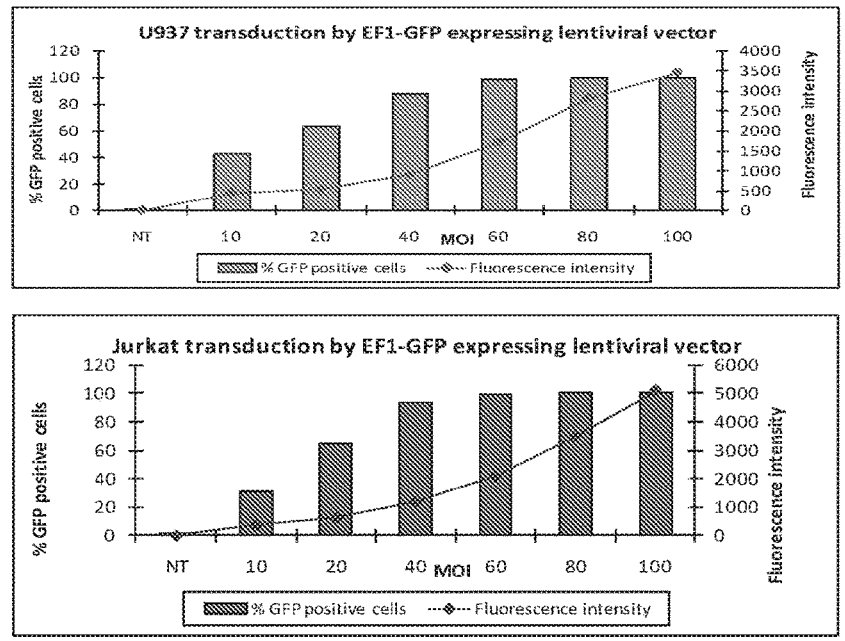
Figure 3A: Cell transduction assay of immortalized cell lines
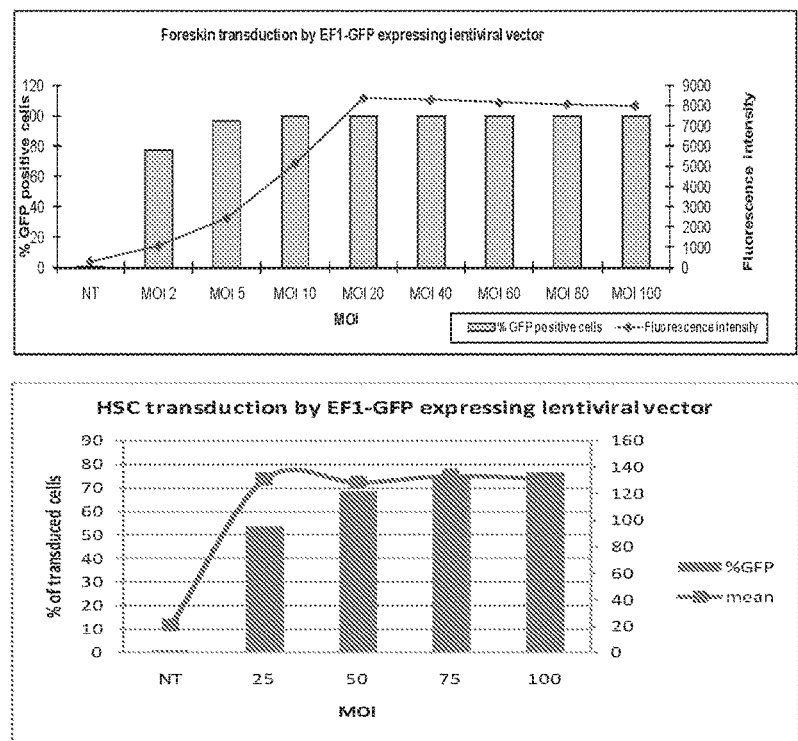
Figure 3B: Cell transduction assay of primary cells

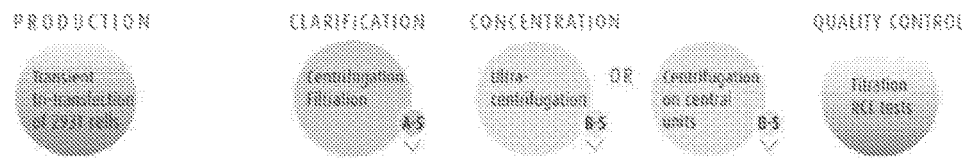
Figure 4A: Commonly vector production with serum by state of art processes
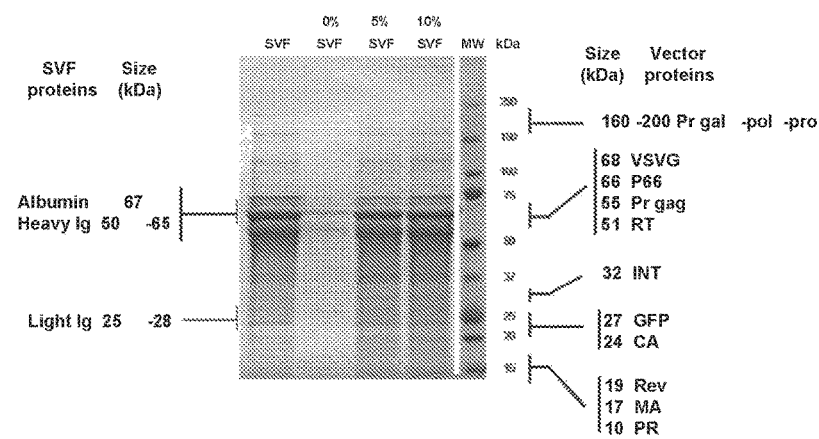
Figure 4B: Evaluation of protein profile according to the FBS rate analyzed by SDS-page gel
| %SVF | Titer (TU/ml)(1) | PP/TU (2) | TU/tot prot (TU/mg) (3) |
|---|---|---|---|
| 10% | 1,20E+06 | 192 | 3,90E+05 |
| 5% | 8,00E+05 | 263 | 3,90E+05 |
| 0% | 1,80E+06 | 161 | 1,90E+06 |
Figure 4C: Summary of batch titers used for evaluating the protein profiles

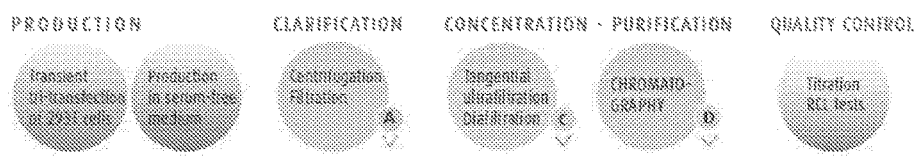
Figure 5A: viral vector concentration and purification processes
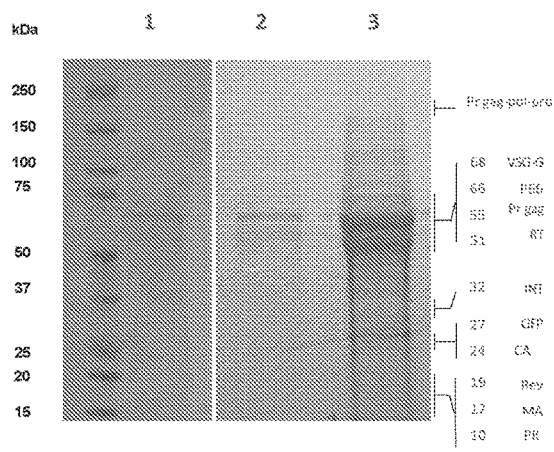
Figure 5B: SDS-page gel of ultracentrifugated and centrifuged on central units vectors (B)

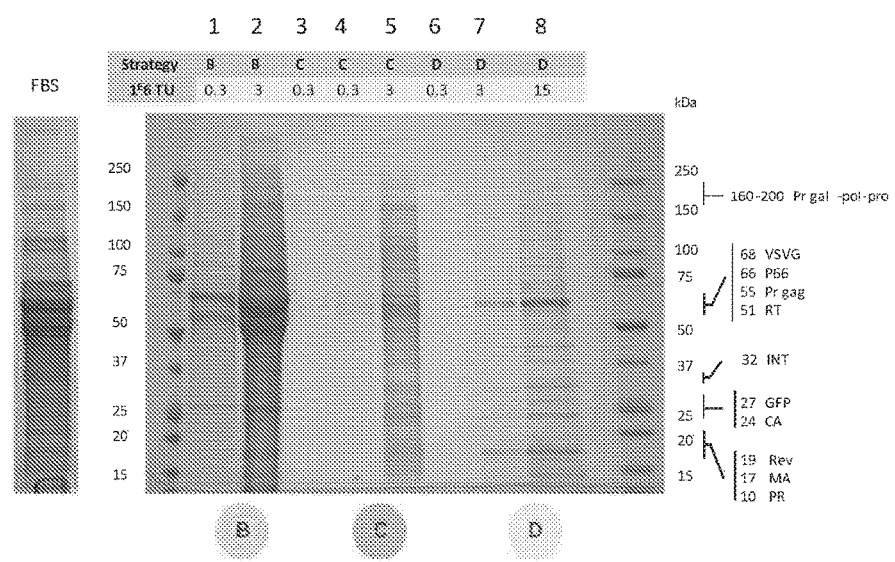
Figure 5C: purification process performances through SDS-PAGE gel analysis

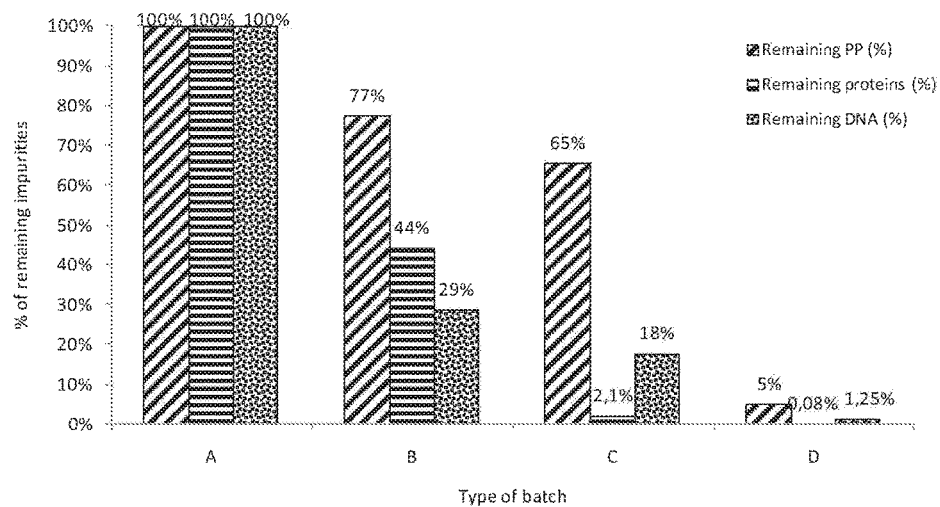
Figure 6: Remaining impurities depending on the Vectalys purification strategies
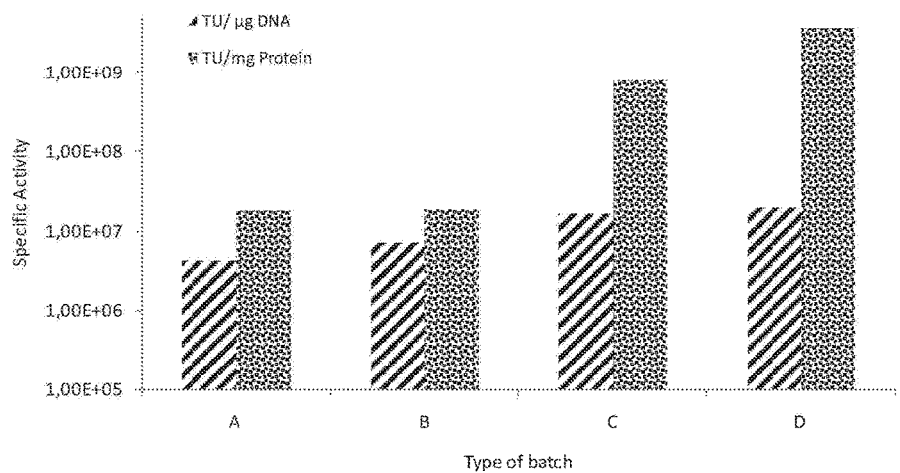
Figure 7: Specific activities of purified biologically active retroviral vectors compared to impurities, depending on the purification strategies

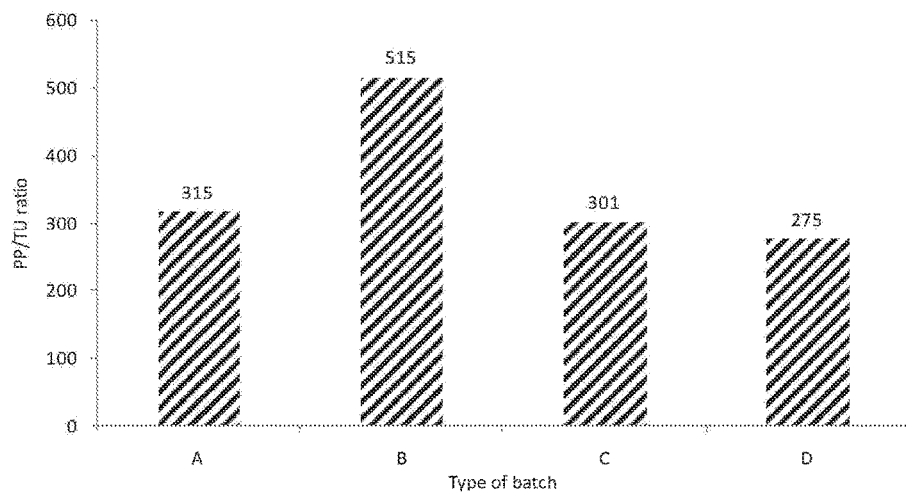
Figure 8: Physical particles - Transduction unit ratio (PP/TU) depending on the purification strategies
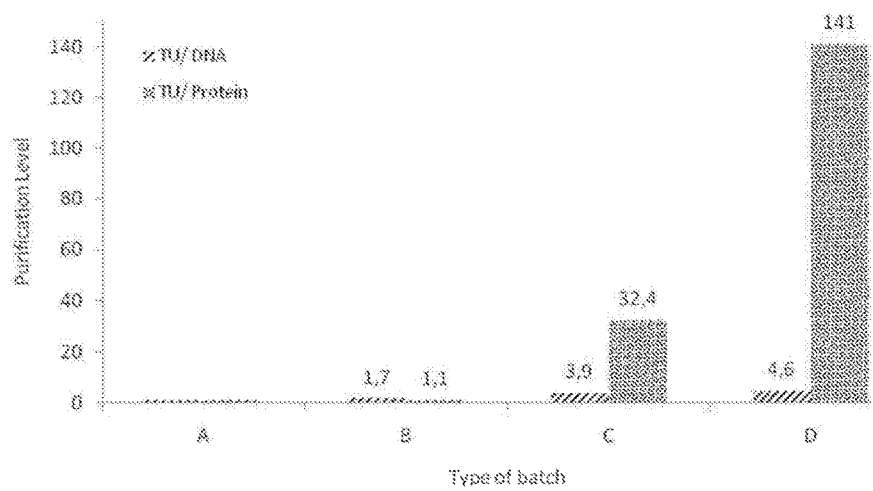
Figure 9: Purification level of purified biologically active retroviral vectors compared to impurities, depending on the Vectalys purification strategies Figure 10: IMR90 cell transduction with non integrative lentiviral vectors (NILV) and integrative lentiviral vectors (ILV)
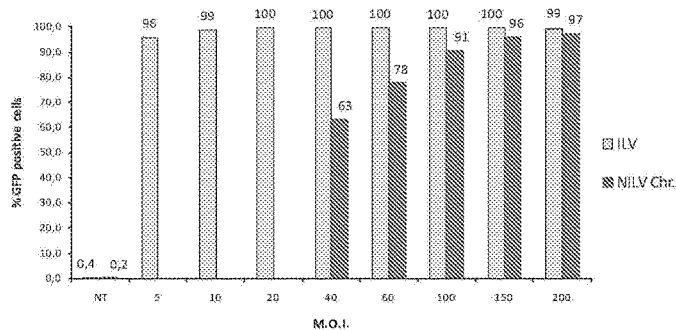
Figure 10A: Percentage of transduced IMR90 cells with GFP expressing ILV and NILV at increasing M.O.I.
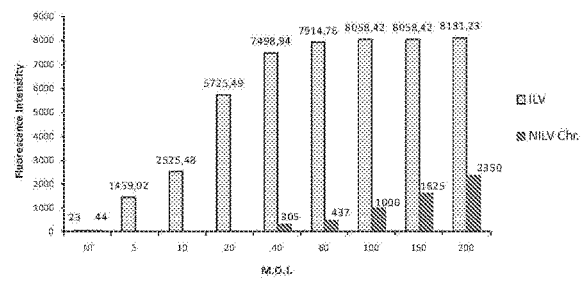
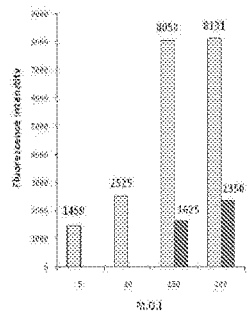
Figure 10B: Fluorescence intensity in transduced IMR90 cells with GFP expressing ILV and NILV at increasing M.O.I.

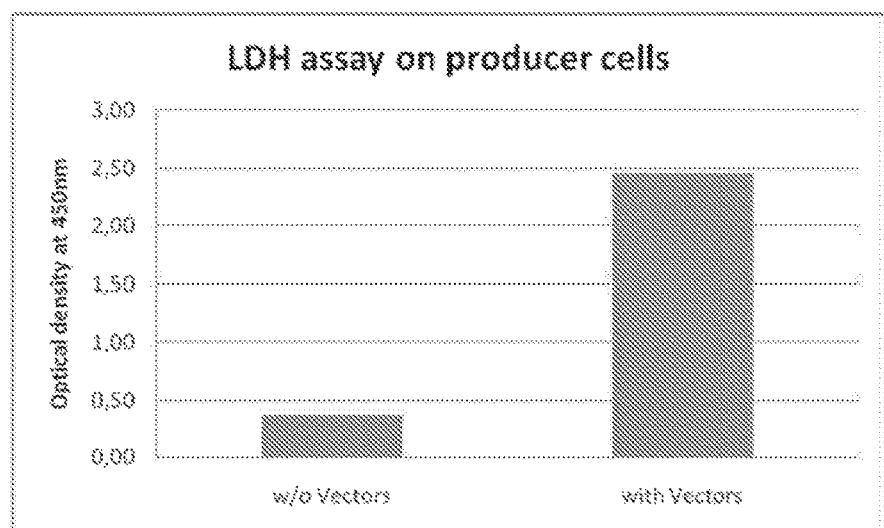
Figure 11: LDH assay in 293T and 293T transfected with the three plasmids used for lentiviral production

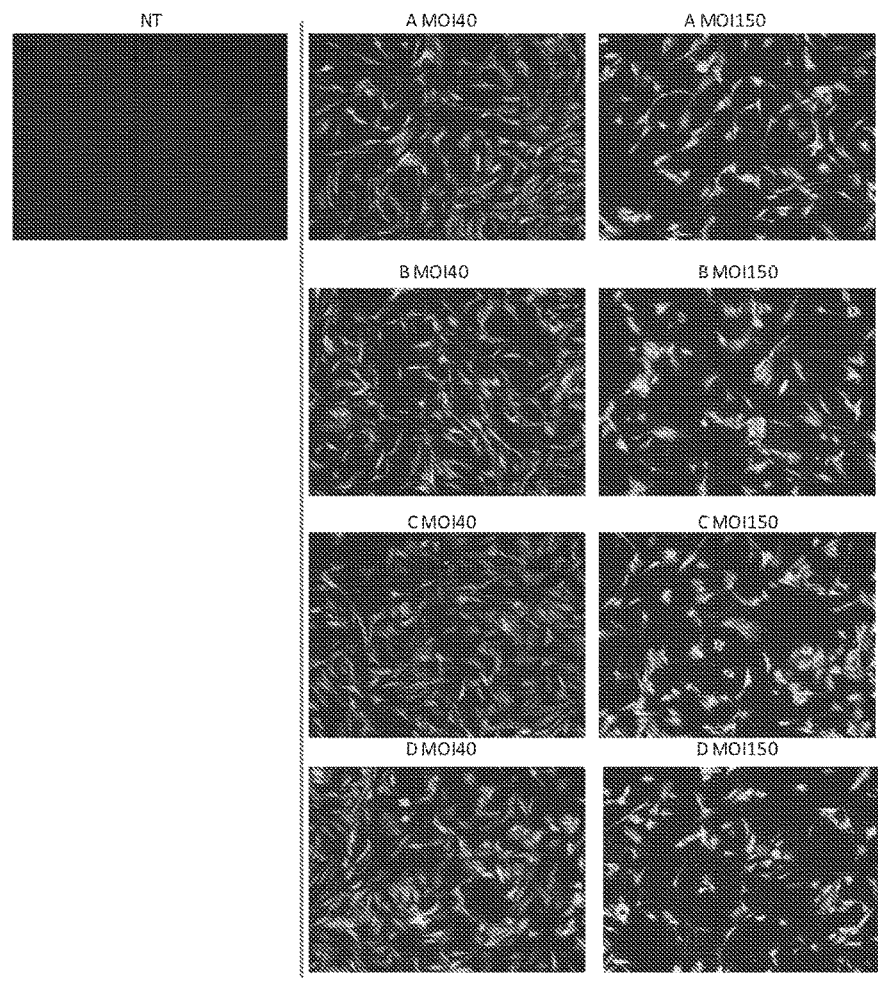
Figure 12A: GFP expression in foreskin cells five days after transduction with a GFP expressing lentiviral vectors (ILV)

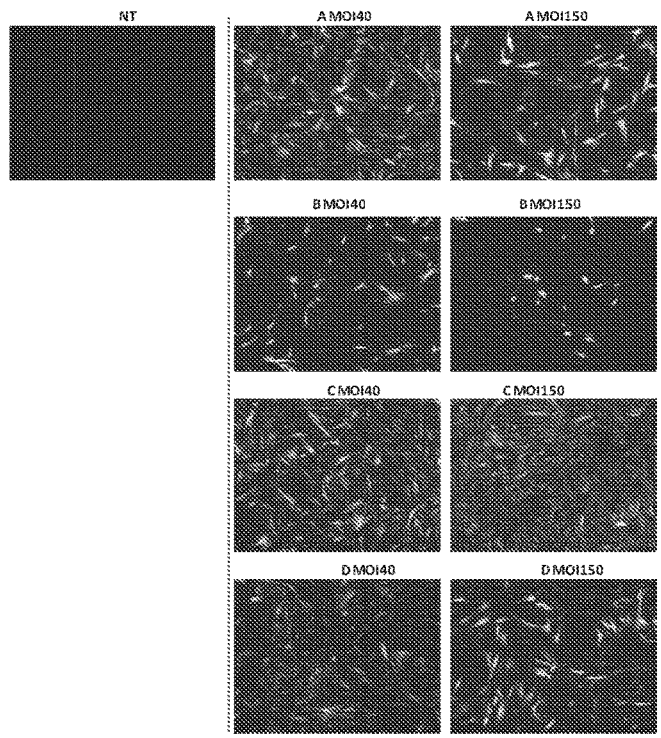
Figure 12B: GFP expression in foreskin cells eleven days afte transduction with a GFP expressing lentiviral vectors (ILV)
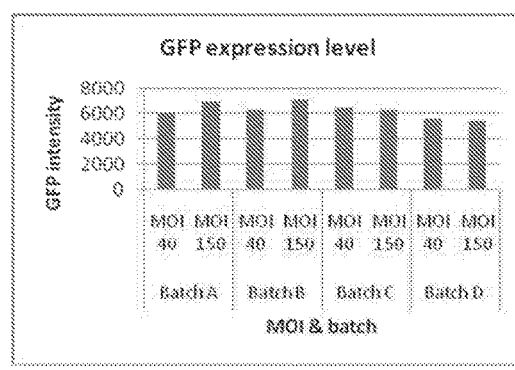
Figure 12C: GFP expression in foreskin cells measured by FACS eleven days after transduction with a GFP expressin lentiviral vectors (ILV)

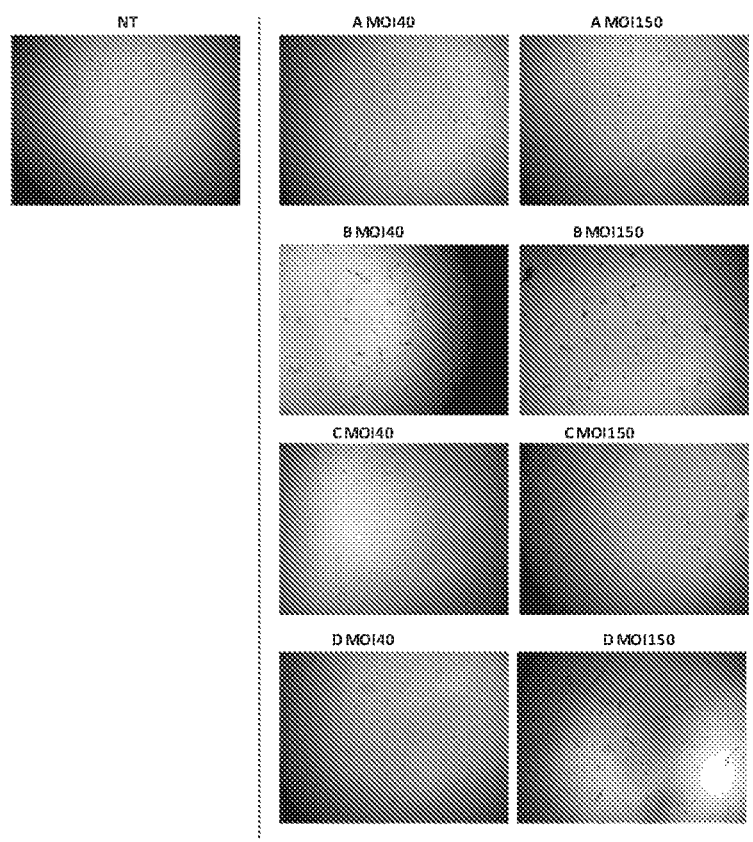
Figure 13: Cell viability 11 days after transduction

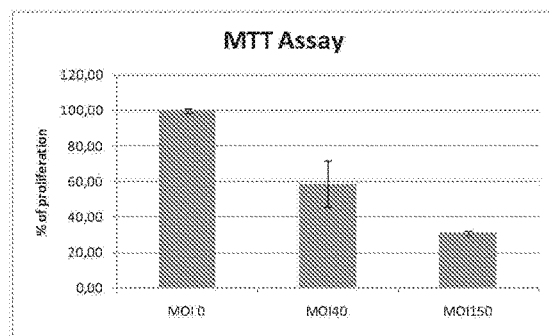
Figure 14A: cell proliferation measured by MTT assay 11 days after transduction with the B batch
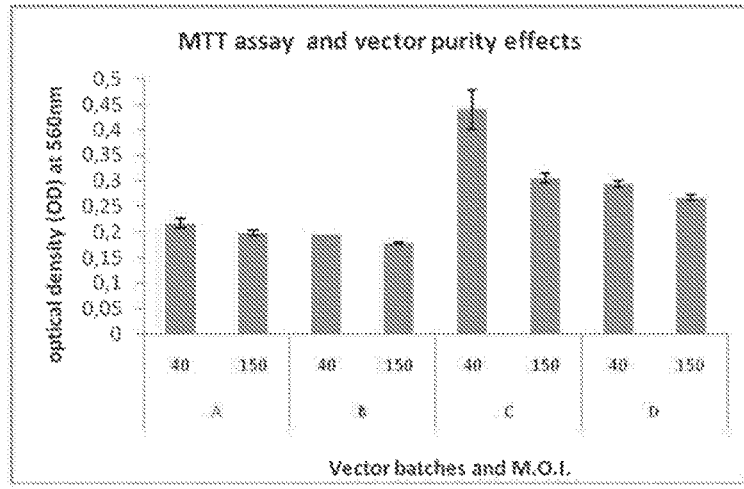
Figure 14B: cell proliferation measured by MTT assay 11 days after transduction with all the batches A, B, C and D

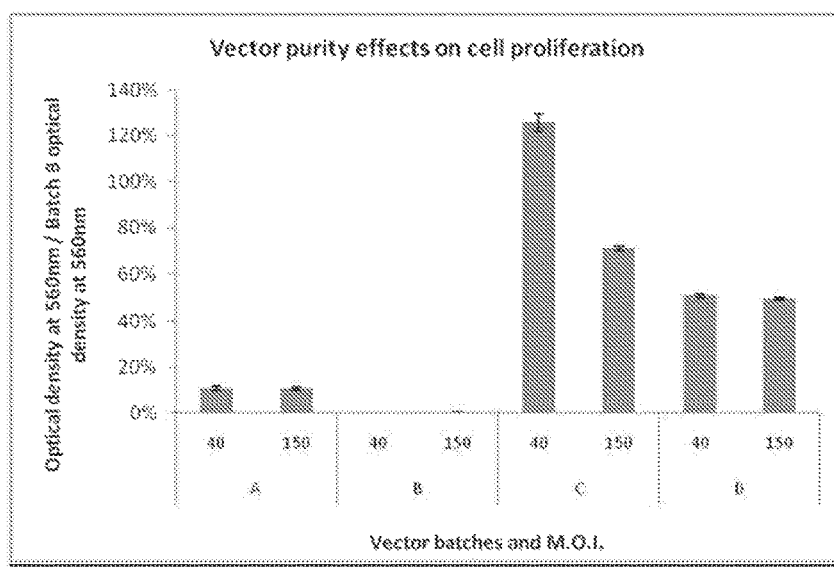
Figure 14C: cell proliferation measured by MTT assay 11 days after transduction with other batches compared to B batch

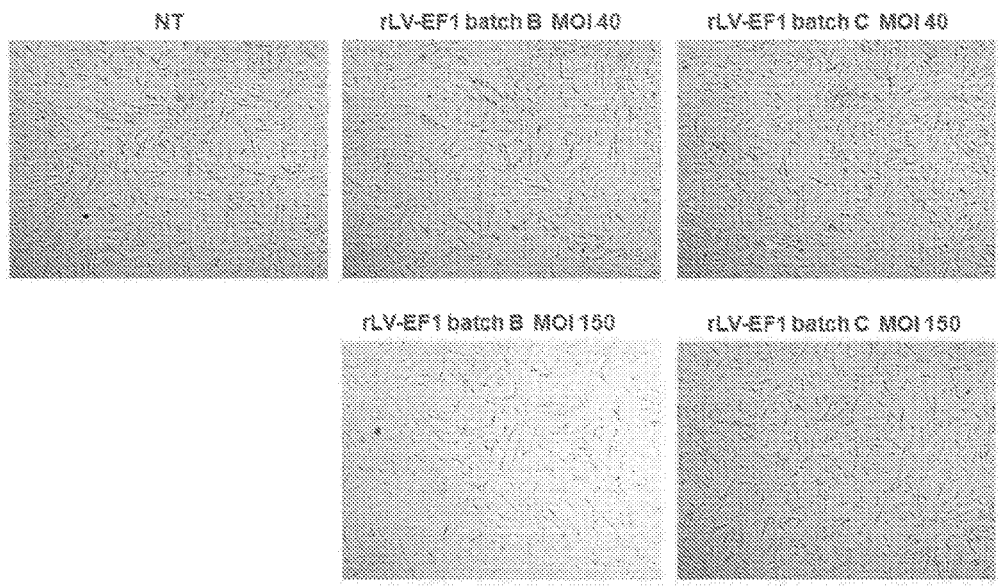
Figure 15A: Foreskin cells growth 48h post-transduction with batch B and C vectors
|  | Titer (TU/mL) (1) | TU / total DNA (TU/µg) (2) | TU / total proteins (TU/mg) (3) | PP/TU (4) |
|---|---|---|---|---|
| rLV-EF1 batch B | 4.7E+08 | 9.1E+06 | 4.3E+07 | 104 |
| rLV-EF1 batch C | 8.9E+09 | 2.0E+07 | 3.7E+08 | 67 |
Figure 15B: Summary of batch B and C titers used for the transcriptomics study

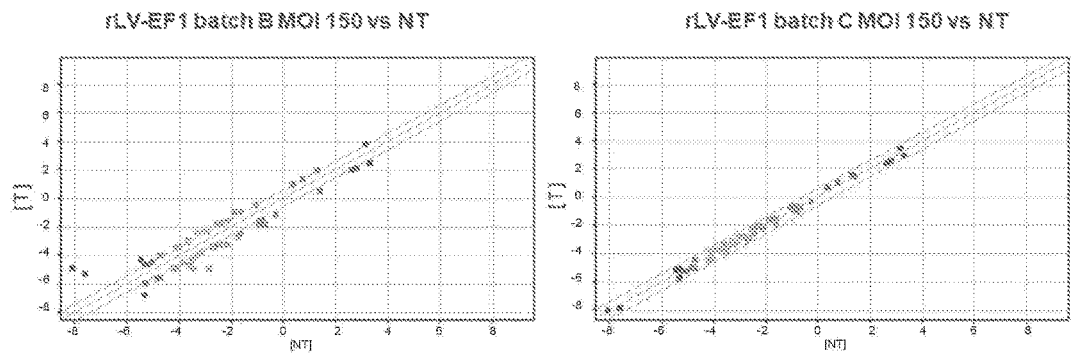
Figure 16A: Scatterplots representing probes specifically impacted with batch B at M.O.I 50
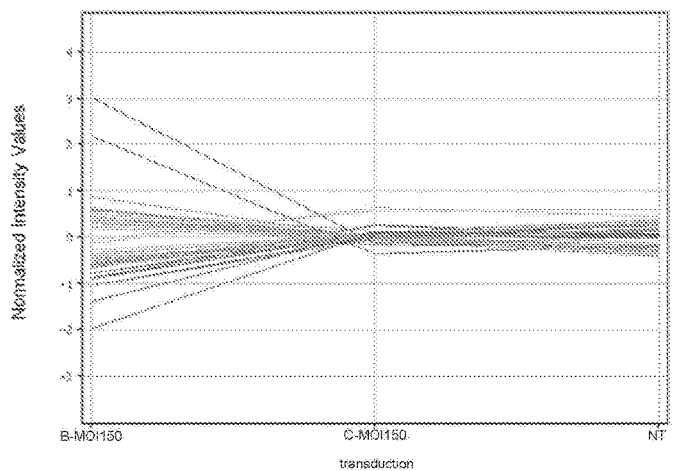
Figure 16B: Profile plot of probes specifically impacted with batch B at M.O.I 150

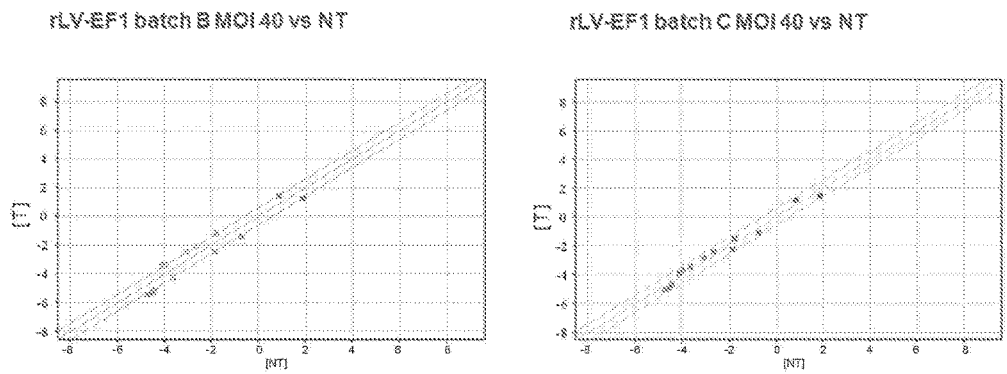
Figure 16C: Scatterplots representing probes specifically impacted with batch B at M.O.I 40
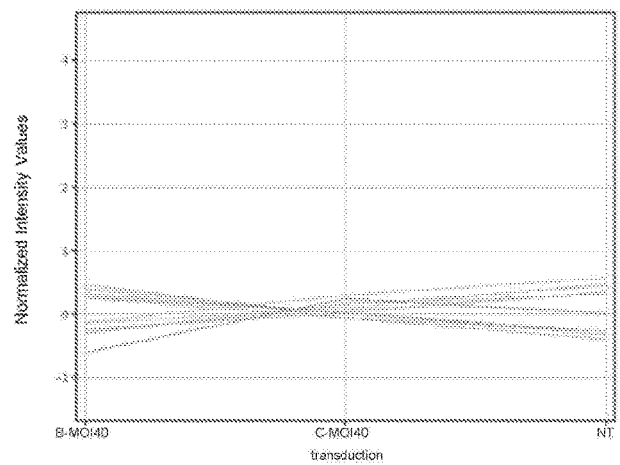
Figure 16D: Profile plot of probes specifically impacted with batch B at M.O.I 40

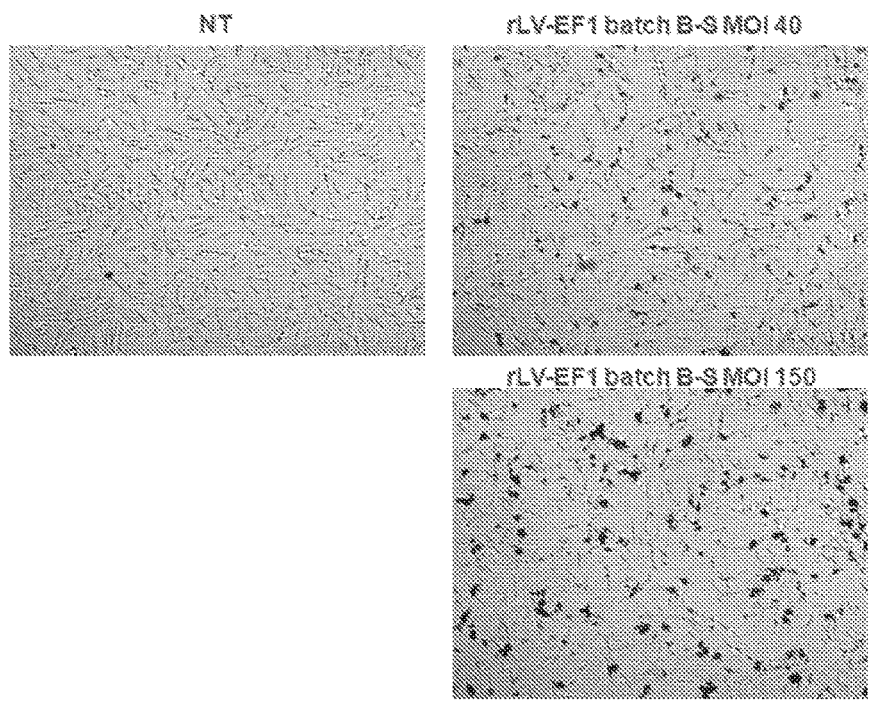
Figure 17A: Cells transduced with batch B-S compared to non-transduced cells
| | Titer (TU/mL) (1) | TU / total DNA (TU/µg) (2) | TU / total proteins (TU/mg) (3) | PP/TU (4) |
|---|---|---|---|---|
| rLV-EF1 batch B-S | 3,3E+07 | 4,7E+05 | 1,1E+05 | 1017 |
Figure 17B: Characteristics of batch B-S used for the transcriptomics study

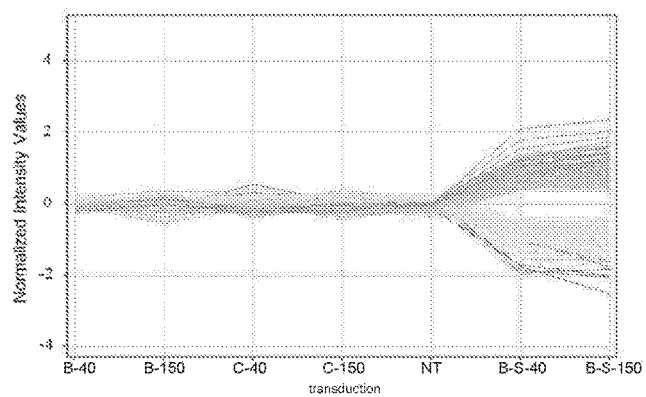
Figure 18: Profile plot representing probes impacted with batch B-S at M.O.I 40 and 150 and not differential with batches B and C

VIRUS-BASED VECTOR COMPOSITIONS USEFUL FOR TRANSDUCING EUKARYOTIC CELLS

CROSS-REFERENCE TO RELATED APPLICATIONS

This application claims priority from U.S. Provisional Patent Application Ser. No. 61/512,289, filed Jul. 27, 2011, the disclosure of which is incorporated herein by reference in its entirety.

INTRODUCTION

The present invention provides viral vector compositions of high titer and purity, as well as methods for production of said compositions and the use of said viral vector compositions for the transduction of eukaryotic cells. The methods of the invention incorporate multiple features, such as production of viral vector particles in serum free media, which provides for enhanced production of said viral vectors. The viral vector compositions of the invention, by virtue of their high titer and purity, minimize the deleterious phenotypic changes that typically occur following transduction of target cells, such as loss of a sub-population of transduced cells, and effects on proliferation, viability and differentiation of transduced cells.

BACKGROUND OF INVENTION

The use of virus-based vectors has become a crucial delivery method for both in vitro applications in drug discovery, in vivo and ex vivo clinical assays and for gene therapy. Viral vectors fall into two main categories: integrating vectors, which insert themselves into the recipient genome and non-integrating vectors, which usually form an extra chromosomal genetic element. Integrating vectors such as gamma-retroviral vectors (RV) and lentiviral vectors (LV) are stably inherited. Non-integrating vectors, such as adenoviral vectors (ADV) and adeno-associated virus (AAV) vectors are quickly lost from cells that divide rapidly. Some factors influencing the choice of a particular vector, include its packaging capacity, its host range, its gene expression profile, its transduction efficiency and its capacity to elicit immune responses, which is particularly problematic if repeated administrations or transductions are needed. Some of these parameters can be adjusted or controlled. One parameter is the use of highly concentrated but also highly purified vectors to allow efficient cell transduction and to avoid specific cell responses due to contents other than the vector itself.

Current methods used to produce and concentrate the virus based vectors are not optimal to preserve the vector integrity and the batch quality. Indeed, small-scale experimental batches are commonly concentrated by simple methods based on ultracentrifugation or centrifugation on ready-to-use central units. Such batches are referred to herein as batches A-Serum (A-S) and B-Serum (B-S) and the processes used to produce such batches is described in FIG. 4A. Those methods also concentrate cellular debris, membrane fragments and proteins secreted by the producer cells and from the culture medium including serum and are unsuitable for producing vector batches under good manufacturing practices (GMP). One major drawback of these batches is their inability to allow high transduction efficiency in a reproducible manner of some non-proliferating cells such as neurons, macrophages or hematopoietic stem cells when using low or medium multiplicity of infection (M.O.I.). Usually, scientists focused on vector pseudotyping or transduction protocol optimizations to improve the transduction efficiency (Janssens et al., 2003) although the use of higher M.O.I. is the clue to reaching high transduction levels. However, since such a batch B-S induces cell toxicity (Selvaggi et al., 1997; Reiser, 2000; Baekelandt et al., 2003), the results of transduction efficiency with this type of product B-S are always a balance between the transduction level and the resulting toxicity on target cells. Furthermore, another drawback of published retroviral or lentiviral vectors concentrated by classical techniques is the inability of transduced stem cells, particularly for hematopoietic stem cells, to progress down differentiation pathways after transduction.

Merten et al. (2010) used a downstream process based on several membrane-based and chromatographic steps but with a production process using a medium with 10% of serum, which is a critical difference between the process of Merten et al. and the process developed according to the present invention. The present invention provides compositions and methods for transduction of cells using retroviral or lentiviral vectors which exhibit a high purity level. Such compositions and methods have no detrimental impact on stem cell differentiation into specialized cells.

The production step has a great impact on the final concentrated product as it provides the starting material to be subsequently subjected to concentration and purification steps. Production might be performed with or without serum, with or without sodium butyrate induction and the supernatant can be harvested either once 48 h after transfection or twice 64 h and 88 h post transfection for example (Cooper et al., 2011). The major disadvantage of such harvesting times is the lack of consideration of the vector particle half life. These conditions have a great impact on the content of initial contaminants (DNA and/or protein contaminants) and the level of toxicity content of the crude supernatant. These elements must be measured to characterize each batch corresponding to a specific process of production, purification and concentration i.e batches A, B, C and D of the present invention. Cooper et al. characterized neither the initial product nor the purified final product by measuring initial contaminants and their removal after concentration/purification process, contrary to the present invention (See Table 1)

The present invention provides a final purified RNA based viral vector composition comprising less than 2% of initial protein contaminants and less than between 70 and 90% of initial DNA contaminants, compared to the crude RNA based viral vector composition as present in the cell serum-free medium, said composition being capable of transducing eukaryotic cells without significantly affecting cell viability.

The present invention provides a purified RNA based viral vector composition comprising less than 2% of initial protein contaminants and less than 30% of initial DNA contaminants, compared to the crude RNA based viral vector composition as present in the cell serum-free medium, said composition being capable of transducing eukaryotic cells without affecting cell viability.

Applicants demonstrate herein that each of these parameters (serum, sodium butyrate induction and vector harvest times) modify the initial crude vector supernatant composition which induces a differential toxicity level on target cells.

SUMMARY OF THE INVENTION

The present invention provides viral vector compositions (also referred to as viral vector particles) of high titer and purity, as well as methods for production of said compositions. The viral vector compositions of the invention, by virtue of their high titer and purity, minimize the deleterious target cell phenotypic changes that typically occur following transduction of target cells.

The present invention provides a purified RNA based viral vector composition comprising less than 2% of initial protein contaminants and less than 70 up to 98.8% of DNA contaminants, compared to the crude RNA based viral vector composition as present in serum-free medium, the crude batch A, said composition being capable of transducing eukaryotic cells without affecting cell viability.

In an embodiment of the invention, a purified RNA based viral vector composition is provided, wherein the removal of DNA contaminants comprises between 60 to 99% compared to the initial contaminants present in the crude RNA based viral vector composition and the removal of proteins contaminants comprises between 55 to 100% compared to the initial contaminants present in the crude RNA based viral vector composition. Thus, the present invention provides a purified RNA based viral vector composition comprising less than 40% of DNA contaminants compared to the initial contaminants present in the crude RNA based viral vector composition and less than 45% of proteins contaminants compared to the initial contaminants present in the crude RNA based viral vector composition.

In another embodiment of the invention, the present invention provides a purified RNA based viral vector composition, wherein the removal of DNA contaminants comprises between 60 to 75% compared to the initial contaminants present in the crude RNA based viral vector composition and the removal of proteins contaminants comprises between 55 to 65% compared to the initial contaminants present in the crude RNA based viral vector composition (Batch B). Thus, the present invention provides a purified RNA based viral vector composition comprising 25% to 40% of DNA contaminants compared to the initial contaminants present in the crude RNA based viral vector composition and 35% to 45% of proteins contaminants compared to the initial contaminants present in the crude RNA based viral vector composition. This purified RNA based viral vector composition can also be used for transducing immortalized cell lines without affecting their viability.

In another embodiment of the invention, the present invention provides a purified RNA based viral vector composition, wherein the removal of DNA contaminants comprises between 70 to 90% compared to the initial contaminants present in the crude RNA based viral vector composition and the removal of proteins contaminants comprises up to 98% compared to the initial contaminants present in the crude RNA based viral vector composition (Batch C). Thus, the present invention provides a purified RNA based viral vector composition comprising 10% to 30% of DNA contaminants compared to the initial contaminants present in the crude RNA based viral vector composition and less than 2% of proteins contaminants compared to the initial contaminants present in the crude RNA based viral vector composition. This purified RNA based viral vector composition can be used for transducing primary and stem cells without affecting their viability.

In another embodiment of the invention, the present invention provides a purified RNA based viral vector composition, wherein the removal of DNA contaminants is up to 98.8% compared to the initial contaminants present in the crude RNA based viral vector composition and the removal of proteins contaminants is up to 99.9% compared to the initial contaminants present in the crude RNA based viral vector composition (Batch D). Thus, the present invention provides a purified RNA based viral vector composition comprising less than 2%, preferentially 1.2%, of DNA contaminants compared to the initial contaminants present in the crude RNA based viral vector composition and less than 1%, preferentially 0.1%, of proteins contaminants compared to the initial contaminants present in the crude RNA based viral vector composition. This purified RNA based viral vector composition can also be used for in vivo injection.

In a specific embodiment of the invention, the crude RNA based viral vector is one wherein the physical particles/transducing units (PP/TU) is comprised of between 200:1 up to 900:1. In yet another embodiment of the invention, the concentrated RNA based viral vector, concentrated by simple methods based on ultracentrifugation or centrifugation on ready-to-use central units, is one wherein the physical particles/transducing units (PP/TU) is comprised of between 200:1 up to 600:1. Still further, the RNA based vector is a concentrated and purified RNA based vector wherein the physical particles/transducing units (PP/TU) is comprised of between 100:1 up to 400:1. Said RNA based vectors, because of their high titer and purity, have little to no effect on cell proliferation, viability, and/or the ability of cells, such as stem cells, to differentiate. The methods described herein provide a means for following the evolution of the ratio PP/TU from the crude batch A to the batches C and D and to ensure that it either decreases or remains stable. An increase in the ratio might prove that the process of concentration damages the vector particles.

The present invention further provides, but is not limited to, a viral DNA construct as contained in a bacterial host as deposited at CNCM Collection under the accession no CNCM 1-4487 (pEnv) or no CNCM 1-4488 (pHIV-Gag/Pol) or no CNCM I-4489 (pLV.EF1.GFP). The invention also provides a purified nucleotide sequence of viral origin inserted in a vector for the production of a RNA based vector according to the present invention, said nucleotide sequence being an insert contained in any of the three recombinant hosts deposited at the CNCM Collection under the accession numbers no CNCM 1-4487 or no CNCM 1-4488 or no CNCM 1-4489.

Such RNA based viral vectors, produced according to the present invention, are capable of transducing eukaryotic target cells for transfer of a nucleic acid of interest (transgene) into said cells. Such transduction methods may be used, for example, in in vitro applications for drug discovery, in in vivo and ex vivo clinical assays, and for gene therapy. The compositions of the invention are especially well suited for transducing cells requiring a high M.O.I (multiplicity of infection).

The methods of the invention incorporate multiple features such as production of RNA based viral vector particles in serum free media which provides for enhanced production of said viral vectors. In one embodiment of the invention, the method of the invention comprises:

(i) transfection of a producer cell, modified to complement deletions in the RNA viral genome upon which the viral vector is based, and culturing the producer cells under suitable conditions to permit the production of RNA based viral vector particles, wherein said culturing following transfection is conducted in serum free medium; and (ii) collecting the supernatant containing said RNA based viral vector particles.

In an embodiment of the invention, the supernatant containing the RNA based viral vector particles may be collected at specific time intervals post transfection said specific time intervals depending on the half life of the vector particles at 37° C., which is typically about 8 hours depending on the producer cell type and culture medium used (Le Doux et al., 1999). This step protects the vector particles from degradation in the cell medium during the production step and the resulting release of vector particle waste in the supernatant.

The method of the invention may further optionally comprise the step of tangential ultrafiltration containing a diafiltration step. In yet another embodiment of the invention, following the tangential ultrafiltration diafiltration step, the method of the invention may further comprise a step of ion-exchange chromatography which is performed to further concentrate and purify the viral vector particles.

In a specific embodiment of the invention, the ultrafiltration is operated on polysulfone hollow-fiber cartridges. Further, the retenate obtained following ultracentrifugation may be treated with an enzyme, such as a nuclease, that is able to degrade contaminating nucleic acids. Such enzymes include, but are not limited to, a benzonase or a DNase. Following product recovery, the viral vector particles can be further purified on a ion-exchange column by adding, for example, DMEM and separation by formation of a salt gradient.

The methods of the invention provide a preparation of purified RNA based viral vector particles wherein the removal of DNA contaminants comprises between 70 to 99% of such contaminants present in the initial serum-free culture medium, and the removal of cellular proteins contaminants comprises between 50 to 99.9% of the cellular proteins contained in the initial serum-free culture medium, and wherein the ratio PP/TU is comprised of between 100 to 900. The quality of the batch increases as the ratio PP/TU decreases. This means that an excess of physical particles with respect to effective particles has a negative effect on the efficiency of transduction and the phenotype of transduced cells. A ratio PP/TU of higher than 1000, as calculated using methods as described herein in the Materials & Methods, is considered as the upper acceptable limit.

The methods of the invention further provide a preparation of purified RNA based viral vector particles, wherein the removal DNA contaminants comprises up to 71% of the content of such contaminants present in the initial serum-free culture medium, and the removal of cellular proteins contaminants up to 56% of the content of such contaminants present in the initial serum-free culture medium, and wherein the ratio of PP/TU comprises between 100 and 600.

The methods of the invention result in the production of purified RNA based viral vector particles capable of transducing target eukaryotic cells without affecting the viability of the cells, their capacity to proliferate in vitro, or their ability to progress down a pathway of differentiation (for example, when transducing stem cells). Such purified RNA based viral vector particles are produced in a cellular free serum system and they can be used for transducing target eukaryotic cells in vitro, said cells being suitable for injection into a host in vivo. Such eukaryotic cells include, for example, immortalized cells, primary cells, stem cells or induced-pluripotent stem cells Accordingly, the present invention provides a method of preparing a genetically modified eukaryotic cell characterized by the steps of contacting an eukaryotic cell with a RNA based viral vector particle, containing a genetic sequence of interest, and prepared according to the present invention. The method may further comprise separating the genetically modified eukaryotic cell from the serum-free culture cell medium supernatant. The serum free medium is important when producing viral vector particles but also when transducing cells like stem cells or primary cells, for example, which may require specific medium and/or serum. Indeed, each of parameters among the presence/absence of serum, sodium butyrate induction or vector harvest times, can affect the initial crude vector supernatant composition and thus result in a differential toxicity level on transfected cells.

BRIEF DESCRIPTION OF THE FIGURES

FIG. 1. Vector production schema. Producer cells are transfected with packaging and expression plasmids to produce non-replicative lentiviral vectors in the cell supernatant.

FIG. 2A. Plasmid harboring gag and pol genes. FIG. 2B. Envelope expressing helper plasmid. FIG. 2C. Transgene expression plasmid.

FIG. 3A. Cell transduction assay of immortalized cell lines. 50,000 cells per well are seeded in 24-wells microplate (Corning CellBind 24 wells-microplate) and mixed with a GFP-expressing lentiviral vector. The optimal transduction conditions is determined using a range of M.O.I. from 10 to 100, in the presence of 4 µg/mL polybren in a total volume of 1 mL, overnight at 37° C./5% $CO_2$. Supernatant is replaced with fresh culture medium after the overnight incubation. Three days after transduction, transduced cells are analysed by flow cytometry. FIG. 3B. Cell transduction assay of primary cells. 50,000 cells per well are seeded in 24-wells microplate (Corning CellBind 24 wells-microplate) and mixed with a GFP-expressing lentiviral vector. The optimal transduction conditions is determined using a range of M.O.I. from 10 to 100, in presence of 4 µg/mL polybren in a total volume of 1 mL, overnight at 37° C./5% $CO_2$. Supernatant is replaced with fresh culture medium after the overnight incubation. Three days after transduction, transduced cells are analyzed by flow cytometry.

FIG. 4A. Common vector production method with serum by state of art processes. FIG. 4B. Evaluation of protein profile according to the FCS rate analyzed by SDS-page gel. 15 µg of total proteins of viral supernatants were loaded on SDS-PAGE gel. Total proteins were quantified by spectrophotometry at 280 nm. FIG. 4C. Summary of batch titers used for evaluating the protein profiles. (1) Transducing units (TU) were determined by flux cytometry. (2) Physical particles (PP) were quantified by HIV-p24 ELISA in order to determine PP/TU ratio. (3) Total proteins were quantified by spectrophotometry at 280 nm.

FIG. 5A. Viral vector concentration and purification process of the present invention. The different processes are sequential (from A to D corresponding to the obtaining of batches A to D) to meet the target cells concentration and purification requirements: immortalized cells (A), primary and stem cells (C) and in vivo injection (D). FIG. 5B. SDS-page gel of ultracentrifugated and centrifuged on central units vectors produced without serum (B). Lane 1: $3 \times 10^5$ TU of ultracentrifugated batch. Lane 2 & 3: respectively $3 \times 10^5$ TU & $3 \times 10^6$ TU of centrifugated on central unit. FIG. 5C. Purification process performances through SDS-PAGE gel analysis. Lane 1: $3 \times 10^5$ TU of ultrafiltered batch using ready to use centrifugation unit (strategy B). Lane 2: $3 \times 10^6$ TU of ultrafiltered batch using ready to use centrifugation unit (strategy B). Lane 3: $3 \times 10^5$ TU of ultrafiltered batch using hollow fibers (strategy C). Lane 4: $3 \times 10^5$ TU of ultrafiltered batch using hollow fibers followed by an additional concentration step using ready to use centrifugation unit. Lane 5: $3 \times 10^6$ TU of ultrafiltered batch using hollow fibers followed by an additional concentration step using ready to use centrifugation unit. Lane 6: 3×10⁵ TU of chromatographied batch (strategy D). Lane 7: 3×10⁶ TU of chromatographied batch followed by an additional concentration step using ready to use centrifugation unit. Lane 8: 15×10⁶ TU of chromatographied batch followed by an additional concentration step using ready to use centrifugation unit.

FIG. 6. Remaining impurities depending on the purification strategies of the present invention. The concentration and purification strategies show different impurities removal profiles depending on the concentration and purification techniques used. From A to D, the remaining impurities (proteins, DNAs and non-biologically viral vectors (PP)) decrease to achieve the FDA purification requirements for in vivo injection (D).

FIG. 7. Specific activities of purified biologically active retroviral vectors compared to impurities, depending on the purification strategies. The viral particles and their contaminants environment are represented by the specific activities. The specific activity is the biological activity of the vectors per milligram of total protein (expressed in TU/mg), or per microgram of residual DNA (expressed in TU/μg), thus giving a measurement of viral vector's activities in their environment. The specific activity increases as contaminants decrease in the vector's environment.

FIG. 8. Physical particles/Transduction unit ratio (PP/TU) depending on the purification strategies of the present invention. Some defects may appear in late stage vector production phases leading to the production of non-infectious viral vectors. Those physical particles devoid of any biological activity have almost the same physico-chemical properties of the biologically active particles causing difficulties in their elimination during the concentration-purification processes.

FIG. 9. Purification level of purified biologically active retroviral vectors compared to impurities, depending on the purification strategies of the present invention. The purification levels represent the purification ratio between viral vectors and impurities, such as proteins or DNA, present in the viral vector environment. The purification level of the four batches increase from batch A to batch D as the remaining impurities into the final recovery product decrease.

FIG. 10. IMR90 cell transduction with non-integrative lentiviral vectors (NILV) and integrative lentiviral vectors (ILV). 50,000 cells per well are seeded in 24-wells microplate and mixed with a the lentiviral vector from M.O.I. 5 to 200, in presence of 4 μg/mL polybren in a total volume of 1 mL, overnight at 37° C./5% CO2. Supernatant is replaced with fresh culture medium after the overnight incubation. Six days after transduction, GFP expression is determined by FACS analysis. FIG. 10A. Percentage of transduced IMR90 cells with GFP expressing ILV and NILV at increasing M.O.I. FIG. 10B. Fluorescence intensity in transduced IMR90 cells with GFP expressing ILV and NILV at increasing M.O.I.

FIG. 11. LDH assay in 293T cells and 293T cells transfected with the three plasmids used for lentiviral production.

FIG. 12A. GFP expression in foreskin cells five days after transduction with a GFP expressing lentiviral vectors (ILV). Batches are related as A, B, C and D letters. 50 000 cells per well are seeded in 24-wells microplate and mixed with a the lentiviral vector at M.O.I. 40 and 150 in presence of 4 μg/mL polybren in a total volume of 1 mL, overnight at 37° C./5% CO2. Supernatant is replaced with fresh culture medium after the overnight incubation. Five days after transduction, cells were fixed. FIG. 12B. GFP expression in foreskin cells eleven days after transduction with a GFP expressing lentiviral vectors (ILV). Batches are related as A, B, C and D letters. 50,000 cells per well are seeded in 24-wells microplate and mixed with a the lentiviral vector at M.O.I. 40 and 150 in presence of 4 μg/mL polybren in a total volume of 1 mL, overnight at 37° C./5% CO2. Supernatant is replaced with fresh culture medium after the overnight incubation. Eleven days after transduction, cells were fixed. FIG. 12C. GFP expression in foreskin cells measured by FACS eleven days after transduction with a GFP expressing lentiviral vectors (ILV). Batches are related as A, B, C and D letters. Foreskin cells are transduced in 96 well plates and transduced one day later. After 11 days, the GFP intensity is measured by FACS in all target cells.

FIG. 13. Cell viability 11 days after transduction. Foreskin cells are transduced in 96 well plates and transduced one day later.

FIG. 14A. Cell proliferation measured by MTT assay 11 days after transduction with the B batch. Foreskin cells are transduced in 96 well plates and transduced one day later with the B batch. Cells were passed to third after 5 days in all wells and after 11 days, the MTT assay is performed. FIG. 14B. Cell proliferation measured by MTT assay 11 days after transduction with all the batches A, B, C and D. Foreskin cells are transduced in 96 well plates and transduced one day later with the B batch. After 11 days, the MTT assay is performed. FIG. 14C. Cell proliferation measured by MTT assay 11 days after transduction with the other batches compared to B batch. Foreskin cells are transduced in 96 well plates and transduced one day later with the B batch. After 11 days, the MTT assay is performed.

FIG. 15A. Foreskin cells growth 48 hours after transduction with an empty cassette carrying lentiviral vector (rLV-EF1) without cDNA, at M.O.I 40 or M.O.I 150. Batch B and C of rLV-EF1 were derived from the same crude harvest. FIG. 15B. Characteristics of rLV-EF1 B and C batches used for the transcriptomics analysis. (1) Transducing units (TU) were determined by qPCR. (2) Residual DNA was quantified using Quant-iT kit PicoGreen dsDNA kit (Life Technologies). (3) Total proteins were quantified by spectrophotometry at 280 nm. (4) Physical particles (PP) were quantified by HIV-p24 ELISA in order to determine PP/TU ratio.

FIG. 16A. Scatterplot representing the set of probes differentially expressed in rLV-EF1 batch B transduced cells at M.O.I 150 versus non-transduced cells and not affected in rLV-EF1 batch C transduced cells at M.O.I 150 versus non-transduced cells. X-axis represents normalized intensities for Non-Transduced (NT) cells, and Y-axis normalized intensities for Transduced (T) cells. Very light grey tone lines are fold change lines representing fold changes values of −1.5, 1 and 1.5. FIG. 16B. Profile plot representing the same set of probes as showed in FIG. 16A after baseline transformation of intensity values. FIG. 16C. Scatterplot representing the set of probes differentially expressed in rLV-EF1 batch B transduced cells at M.O.I 40 versus non-transduced cells and not affected in rLV-EF1 batch C transduced cells at M.O.I 40 versus non-transduced cells. X-axis represents normalized intensities for Non-Transduced (NT) cells, and Y-axis normalized intensities for Transduced (T) cells. Very light grey tone lines are fold change lines representing fold changes values of −1.5, 1 and 1.5. FIG. 16D. Profile plot representing the same set of probes as showed in FIG. 16C after baseline transformation of intensity values.

FIG. 17A. Foreskin cells 48 hours after transduction with an empty cassette carrying lentiviral vector (rLV-EF1) produced in the presence of serum at M.O.I 40 and 150. FIG. 17B. Characteristics of batch B-S of rLV-EF1 used for the transcriptomics study. (1) Transducing units (TU) were determined by qPCR. (2) Residual DNA was quantified using Quant-iT kit PicoGreen dsDNA kit (Life Technologies). (3) Total proteins were quantified by spectrophotometry at 280 nm. (4) Physical particles (PP) were quantified by HIV-p24 ELISA in order to determine PP/TU ratio.

FIG. 18. Profile plot representing the set of probes specifically differential with rLV-EF1 batch B-S compared to non-transduced (NT) and not impacted with rLV-EF1 batch B and C versus NT (at M.O.I 40 and 150). A baseline transformation was applied on intensity values before representing data. Lines are colored according to their normalized intensity in condition batch B-S M.O.I 150.

DETAILED DESCRIPTION OF THE INVENTION

Table 1: Performances of related products of this invention obtained with the state of the art concentration process (corresponding to the obtaining of batch B) and the processes described in this invention (A, C and D) at a glance. This Table summarizes the batch features described in this invention, depending on the concentration and purification processes. Process B (corresponding to the obtaining of batch B) represents the state of the art process. Transduction using vectors from this process leads to cell viability and proliferation issues. C and D are the processes (corresponding to the obtaining of batches C and D) developed in this invention to answer the cell viability drawbacks observed after transduction using vectors from process B (corresponding to the obtaining of batch B). Batch A was considered as a reference for all the percentage data (process recovery, proteins and DNA removal) in this Table. Batch A is considered an optimized batch since it was produced in a serum free medium, without sodium butyrate induction and harvested at different times based on the half life specific to the viral particle of interest.

Table 2: Measures of contaminants in all the batches A, B, C and D and of efficacy.

Table 3. Impact of harvests times, sodium butyrate induction on transfected producer cells and on the resulting crude vector composition.

The present invention provides a novel process for production of viral vector compositions (also referred to herein as viral vector particles) of high titer and purity. As described herein, a new process has been developed for both vector production and concentration (FIG. 5A). The process is based first on the transient transfection of eukaryotic cells in a serum-free medium which results in the production of a crude batch referred to as batch A (FIG. 5A) which exhibits high quality performance as compared to a batch produced with serum (Batch A-S as described in FIG. 4). This crude supernatant (batch A) is optimized because it is produced without sodium butyrate induction, without serum and collected at specific times post-transfection depending on the half life of the vector particles at 37° C., which is about 8 hours, depending on the producer cell type and the culture medium (Le Doux et al., 1999). The production step is followed by the concentration through ultrafiltration and the purification of vector particles by ion-exchange chromatography and leads respectively to the batches referred to herein as batches C or D and which exhibit a high rate of protein and DNA removal (Tables 1 and 2). The products, batches C and D, can be obtained for small and large scale applications and allow for efficient transduction with no significant effect on cell viability and proliferation as measured by the existing available methods. Such efficient transduction requires methods, as provided herein, for efficient vector production, concentration and purification while maintaining vector potency without introducing cell and media contents that may interfere with the target cell division and metabolism (FIG. 5A).

The method of the invention for production of RNA based viral vectors comprises:

(i) transfection of a producer cell, modified to complement deletions in the RNA based viral genome upon which the vector is based, and culturing under suitable conditions to permit the production of RNA based viral vector particles, wherein said culturing following transfection is conducted in serum free medium; and (ii) collecting the supernatant containing said RNA based viral vector particles.

Said collection can be performed in a sequential manner, depending on the vector particle half life at 37° C., wherein intermediate harvests are performed. This is in contrast to the prior art vector harvesting classically performed by two steps, for example, after transfection as Cooper et al. (2011) and Merten et al. (2010). In an embodiment of the present invention, several harvests may be performed during the 72 h following transfection of the producer cell. In a non-limiting embodiment of the invention, between three to six vector harvests may be performed following transfection depending of the method of transfection and the producer cell line. In a specific embodiment of the invention four harvests at specific intervals following transfection of the producer cell are performed. The interval time between harvest is based on the vector half life at 37° C. in the medium of the producer cell line. The resulting regular interval times are a balance between the requested crude vector functional titre (>$10^6$ TU/ml) and the presence of contaminants able to induce a toxicity in the transfected cells.

In the process of the invention, producer cells are transfected with a viral vector of interest. The viral vector is designed to express a nucleic acid of interest (also referred to herein as a transgene) inserted in the viral nucleic acid upon introduction into a target host cell, either in vivo or in vitro. Such introduction into the target host cell may be used, for example, in drug discovery or gene therapy applications.

Transfection is defined to be the process of deliberately introducing nucleic acids into cells. The term is used strictly for non-viral methods in eukaryotic cells. Transfection is used in the process of viral vector production when gag-pol and env expressing plasmids are transfected on producer cells to get viral vectors in the supernatant. Transduction is the process of deliberately introducing nucleic acids into cells. The term is used for viral based methods in eukaryotic cells. Viral vectors are harvested from the producer cells and are contacted with the eukaryotic cells to obtain the finally transduced cells.

In a preferred embodiment of the invention, the viral vectors are based on viruses belonging to the Retroviridae family that comprises enveloped RNA viruses including, for example, lentiviral (LV) and gamma-retroviral (RV) vectors. The development of a purification process demands an acute knowledge of the physical, chemical and biological properties of vectors. Retroviral vectors are derived from viruses belonging to the Retroviridae family that comprises enveloped RNA viruses with a complex macromolecular structure having an hydrodynamic diameter of approximately 150 nm (Salmeen et al. 1975). Due to the large size the viral particles have low diffusivity (10-8 cm$^2$/s); their density is about 1.15-1.16 g/cm$^3$ as determined by sucrose gradient ultracentrifugation (Coffin et al. 1997). They are composed by 60-70% protein, 30-40% lipid (derived from the plasma membrane of the producer cells), 2-4% carbohydrate and 1% RNA (Andreadis et al. 1999). Retroviral particles consist of two identical copies of single-stranded positive sense RNA, plus integrase and reverse transcriptase enzymes, contained within a protein capsid surrounded by a lipid bilayer membrane. The lipid bilayer is studded with glycoprotein projections. Retroviral vectors are negatively charged particles in a broad pH range since their isoelectric point occurs at very low pH values. The envelope proteins and the lipid bilayer are probably the main contributors to the negative charge at the virus surface (Rimai et al. 1975).

The types of producer cells to be transfected will depend upon the viral vector that has been chosen for use in the practice of the invention. Such cells include any easily transfectable mammalian cells, such as, for example, 293T or HeLa cells. In a preferred embodiment of the invention, when using viral vectors derived from the retrovirus family, such as gamma-retroviral vectors (RV) and Lentivirus vectors (LV), 293T cells may be used. The types of cells to be used in conjunction with a viral vector of interest are known to those of skill in the art.

The producer cells are engineered to express either transiently, or stably, any viral proteins, the expression of which is necessary for assembly and packaging of the viral vector into a virus particle. In an embodiment of the invention, retroviral vectors including lentiviral vectors are produced by cell lines that are engineered to express the vector (which encodes the transgene) and helper constructs (encoding the viral proteins) as described in FIG. 1. To minimize recombination events and the production of replication-competent retroviruses, the retroviral genome sequences may be divided into three different constructs (FIG. 2A-C).

The first construct, the gag-pol vector, encodes the structural proteins and viral enzymes. Respectively, gag is coding for the matrix proteins (MA), the capsid (CA) and the nucleoprotein (NC) structures and pol is coding for the reverse transcriptase (RT) and integrase (IN) enzymes. Most preferably, the viral gag and pol genes are derived from retrovirus preferably a Lentivirus, and most preferably from HIV.

The second construct, the env vector, encodes the envelope proteins from which are derived the surface (SU) and transmembrane (TM) component by disulfide bonds. The TM component is anchored by a transmembrane segment and cannot be removed from the vectors without their disruption (Coffin et al. 1997). The env gene can be derived from any virus, including retroviruses. The env may be amphotropic envelope protein which allows transduction of cells of human and other species, or may be ecotropic envelope protein, which is able to transduce only mouse and rat cells. Further, it may be desirable to target the recombinant virus by linkage of the envelope protein with an antibody or a particular ligand for targeting to a receptor of a particular cell-type. By inserting a sequence (including regulatory region) of interest into the viral vector, along with another gene which encodes the ligand for a receptor on a specific target cell, for example, the vector is now target specific. Retroviral vectors can be made target specific by inserting, for example, a glycolipid, or a protein. Targeting is often accomplished by using an antibody to target the retroviral vector. Those of skill in the art will know of, or can readily ascertain without undue experimentation, specific methods to achieve delivery of a retroviral vector to a specific target. Examples of retroviral-derived env genes include, but are not limited to: Moloney murine leukemia virus (MoMuLV), Feline Immunodeficiency virus (FIV), Harvey murine sarcoma virus (HaMuSV), murine mammary tumor virus (MuMTV), gibbon ape leukemia virus (GaLV), human immunodeficiency virus (HIV) and Rous Sarcoma Virus (RSV). Other env genes such as Vesicular stomatitis virus (VSV) (Protein G) can also be used.

The vector providing the viral env nucleic acid sequence is associated with regulatory sequence, e.g., a promoter or enhancer. Preferably, the regulatory sequence is a viral promoter. The regulatory sequence can be any eukaryotic promoter or enhancer, including for example, the Moloney murine leukemia virus promoter-enhancer element, the human cytomegalovirus enhancer (as used in the illustrative example). In some cases, such as the Moloney murine leukemia virus promoter-enhancer element, these promoter-enhancer elements are located within or adjacent to the LTR sequences.

A third construct, the vector transgene, provides the cis-acting viral sequences necessary for the viral life cycle (FIG. 2C). Such sequences include the psi packaging sequence, reverse transcription signals, integration signals, viral promoter, enhancer, and polyadenylation sequences. This third vector also contains a cloning site for a heterologous nucleic acid sequence to be transferred to a target cell. A schematic illustration of a suitable vector is shown in FIG. 2C with the GFP as a transgene but which can be replaced by any gene or sequence of interest such shRNA (short hairpin RNA or miRNA (micro RNA).

This construct may contain other expression elements like a wild type WPRE sequence (Zufferey et al. 1999), a cPPT/CTS element (Manganini et al., 2002). The gene encoding the beta lactamase is used to select bacteria transformed with these plasmids in order to produce the plasmids. After transfection of the producer cells with these plasmids, the transcription is initiated from the eukaryotic promoter (RSV U3) to the polyadenylation site (HIV1 R) and does not include the gene encoding the beta lactamase. Neither the betalactamase protein nor the corresponding RNA are expressed in the producer cell line or are encapsidated into the vector particle.

Viral pathogenicity is eliminated by substituting genome regions required for retroviral replication by the transgene. This ensures that the genome packaged into the retroviral vectors encodes only transgene and sequences required for packaging and reverse transcription.

The separation of the three retroviral constructs allows pseudotyping of the retroviral vectors with surface proteins from other viruses, thus broadening the viral tropism. The retroviral vectors as described herein, in a non-limiting embodiment, have been pseudotyped with vesicular stomatitis virus G protein (VSV-G) (Clapham, P. et al., 1984). Retroviral vectors pseudotyped with VSV-G protein enter the cells via interaction with widely distributed lipid component of the plasma membrane, thus allowing a very broad spectrum of transduction (Verhoeyen et al. 2004 and Yee et al. 1994). Pseudotyping can have a large impact on the production and purification of retroviral vectors due to alteration of the envelope structure, thus affecting the physico-chemical membrane properties of retroviral vectors used during downstream process.

Producer cells may be transfected with vector constructs according to standard techniques well known to a person skilled in the art. Such techniques include, for example, the calcium phosphate technique, the DEAE-dextran technique, electroporation, methods based on osmotic shock, microinjection or methods based on the use of liposomes. In a preferred embodiment of the invention, the cells may be transfected using a calcium precipitation method. Such a method is preferred when 293T cells are the producer cells of choice but equivalent cells may also be used.

Following transfection, the cells are incubated in serum free media for a time sufficient to allow for the efficient production of viral particles. Serum free media is defined as growth medium for mammalian cell culture substantially free of animal derived sera. Serum free media are well known in the art (Bruner et al. 2010). The incubation time following transfection, will depend on a combination of factors including, for example, the type of viral vector used and the producer cell line of choice. During the time interval following transfection, i.e., incubation time, multiple vector harvests ma be performed. In a preferred embodiment of the invention four vector harvests may be performed. To determine, the most productive incubation conditions, small batch experiments may be performed to determine optimized conditions for generating the highest titre and purest batch of viral particles.

The initial culture supernatant, containing viral vector particles, is referred to herein as, batch A. The method of the invention may further comprise the step of tangential ultrafiltration diafiltration of the batch A product for further purification of viral vector particles. Such an ultrafiltration diafiltration step is a type of membrane filtration in which hydrostatic pressure forces a liquid against a semi-permeable membrane. Suspended solids and solutes of higher molecular weight than the membrane cut off are retained, while water and lower molecular weight than the membrane cut off solutes pass through the membrane. In a preferred embodiment of the invention, ultrafiltration technique is carried out by tangential flow ultrafiltration using polysulfone hollow-fiber cartridges. Such a technique allows for monitoring and adapting the pressure to ensure the maintenance of vector integrity and viability. Such a step provides for concentration of the vector particles, as well as acting as a purification step for removal of initial contaminants, such as host cell proteins and nucleic acids, from the collected batch. Such a batch is referred to herein as batch C.

In yet another embodiment of the invention, following the tangential ultrafiltration and/or diafiltration step, the method of the invention may further comprise the step of ion-exchange chromatography which may be performed to further concentrate and purify the viral vector particles. Such a batch is referred to herein as batch D.

The present invention concerns the use of the composition of batch A on permissive immortalized cell lines such as, for example, HCT116. Further, the present invention concerns the use of the compositions of batches C or D in gene therapy applications which are demonstrated to induce no, or minor cell phenotypic changes, due to the conditions of preparation of the vectors or the conditions of cell cultures in comparison with the prior art product of batch B-S as described in FIG. 4. As set forth herein, the use of ultrafiltration on crude batches without serum allows one to not only concentrate vector particles but also to purify them by removing more that 70% of initial contaminants, such as host cell proteins and DNA used for transfection (Table 2 and 3) from the collected batch. Since the downstream concentration and purification steps are directly affected by changes in the cell culture methods during vector production, it is preferred that both cell culture and concentration/purification steps are conducted in parallel. The removal of serum from the culture medium of the producer cells has a strong impact on the steps of ultrafiltration and chromatography since the initial protein and DNA contents are completely different in crude batches produced with or without serum. Merten et al. (2010) used a downstream process based on several membrane-based and chromatographic steps but with a production process using a medium containing 10% of serum, which is a critical difference between the process developed according to the present invention and the prior art process of Merten et al. (2010). In the crude supernatant of Merten et al. (2010), the initial total protein concentration was about 6 mg/ml while it is 0.14 mg/ml in the present invention without serum, a difference of a factor 40. As described herein, the final concentration of proteins in the batches C and D are less than 0.061 mg/ml and 0.01 mg/ml after respectively ultrafiltration and chromatography while it reaches an average of 1.5 mg/ml after several membrane-based and chromatographic steps on a batch produced with serum (Merten et al., 2010), a respective difference of a factor 25 and 150.

The lack of serum in the crude batch may explain the difference obtained in vector concentration and contaminants removal obtained in the present invention and preliminary studies with these methods for virus or vectors purification (Grzenia et al., 2008). Grzenia et al. observed difficulties because some smaller damaged virus particles and viral fragments were likely deposited on the membrane surface. The efficiency of purification seems to lie in the balance between the molecular weight cut off of the membrane, the ionic strength, the transmembrane pressure (TMP) and the size of the vector. The present invention demonstrates that another parameter that can interfere in the purification process is based on the initial medium content that can influence the removal of host DNA and proteins from the crude batch. As described herein, a combination of cell culture, concentration and purification steps allow for high recovery of viral particles, such as lentiviral or retroviral based particles, which are associated with high purity. Vectors produced according to the invention, with a high quality level permits iPS (induced pluripotent stem cell) generation without effects on cell proliferation during the reprogramming process due to serum contents or medium contaminants, as disclosed in WO 2007/09666 and WO 2009/13971.

The present invention is based on the investigation of the protein and DNA contents associated with particle quantification in physical particles (PP), or biological particles able to transduce cells (TU) after each step of the process of the invention (corresponding to the obtaining of batches A, C and D) in comparison with the commonly used prior art concentration methods (corresponding to the obtaining of batch B). In parallel, the toxicity and proliferation in the transduced cells was evaluated to determine the phenotypic consequences of concentration and purification methods on cells.

The present invention provides compositions comprising high titre and highly purified viral particles which can be used to transduce cells. The compositions of invention provide a means for transduction of delicate or fragile cells, such as primary cells and stem cells, when the use of large medium volume or high multiplicity of infection (M.O.I.) is required. The compositions are therefore suitable for the use of Non Integrating Lentiviral Vectors (NILV) on delicate and fragile cells, which usually require high M.O.I. transduction.

The present invention demonstrates that efficient production of virus-based particles for drug discovery and gene therapy applications requires the development of both robust concentration operations and purification steps as well as the use of adapted media to cultivate the cells and to resuspend the vector batch that will be used to transduce the cells. As demonstrated herein, target cell transduction efficiency depends not only on the cell type (immortalized, primary and stem cells), or the tissue of origin, but also on the vector characteristics (titre, purity level, proteins and DNA contents).

Retroviral vector preparations are not only defined by the viral particles themselves, but also by their close environment, influencing the quality level of the final viral vectors preparation and as demonstrated here the transduction level and the cell viability.

Retroviral vectors are complex macromolecular assemblies of proteins, lipids and RNA, in a cellular culture media containing proteins and DNA contaminants. Therefore, evaluation of such environment can be difficult. Most of the difficulty arises from the incorporation of producer cells components, mostly proteins, during the budding process, both within the lipid bilayer and inside the viral particle. All these characteristics greatly increase the difficulty in determining which sample components are associated with the vector and which are indeed contaminants in the supernatant. The most relevant supernatant contaminants are (i) non-infectious physical particles (PP), (ii) cellular or viral proteins, and (iii) DNA.

Protein impurities are the most abundant contaminants in retroviral vector supernatants. They mostly arise from producer cells protein secretion and the proportion of stress proteins increases while performing a serum free process. Retroviral vectors incorporate host cell proteins during budding, complicating the distinction between contaminant and vector associated proteins. In this study, the viral particles and their protein environment are represented by their specific activities. The specific activity is the biological activity of the vectors per milligram of total protein (expressed in TU/mg), thus giving a measurement of viral vector activities in the cell medium composition. The specific activity increases as contaminants decrease during the purification process as described in the present invention.

DNA contaminants are also found in retroviral vector supernatants. The concern regarding nucleic acid contamination arises from the possibility of cellular transformation events in the target cells as well as cellular inflammation in in vivo treatments. Contamination DNA limits are usually dependent on transduction targets and applications. The different sources of contaminating DNA are the host producer cells and the plasmids from transient transfection used in the production of retroviral vectors. Accordingly, DNAses can be introduced (e.g. BENZONASE®-from Merck, Germany) in the purification process to reduce DNA contamination. The viral particles and their DNA in the cell medium are represented by their specific activities. The specific activity is the biological activity of the vectors per microgram of residual DNA (expressed in TU/µg). As mentioned previously, the specific activity increases as contaminants decrease during the purification process as described in the present invention.

As with wild type viruses, not all of the produced viral particles in a preparation are infectious. In fact, some defects appear in late stage vector production phases. Typically, the particle assembly, the encapsidation, the viral RNA packaging or the budding can lead to some physical abnormalities. Therefore, viral particles without stranded RNAs, with disrupted or non-existent capsid proteins, or with missing envelope proteins are typically produced along with infectious vectors. Those physical particles devoid of any biological activity have almost the same physico-chemical properties as the biologically active particles causing difficulties in their elimination. According to the invention, the ratio of physical to infectious or transducing particles (PP/TU) is considered as optimal when the ratio is comprised between:

900:1 and 200:1, for a crude batch A, preferably less than 600;
600:1 and 200:1, for a batch C, preferably 300:1 or less;
400:1 and 100:1, for a batch D, preferably less than 300:1.

The increase of the ratio PP/TU before and after a concentration step, as observed for process B (corresponding to the obtaining of batch B), means that the process damages the vector particles. This ratio represents a relevant index of purity for several reasons. First, it gives a picture of the vectors state in the crude supernatant and its evolution shows the impact of the process used to concentrate and purify the vectors on their integrity. As it increases, the process damages the particles. In the process described in this invention, the crude titer exhibits a ratio PP/TU comprised between 500 and 900 although a large number of studies obtained a ratio greater than 1000 or more. Merten et al., (2010) gives a ratio of 2333 in a batch containing 10% serum and harvested 2 times each 24 h after transfection. This number is calculated following the formula described below:

PP/TU=$(4.9\times10^4$ ng P24/ml$\times10^7$ PP/ng P24$)/4.3\times10^3$ IG/ml as calculated in Merten et al. 2010. One nanogram of P24 represents $10^7$ PP and the efficient titer calculated in integrated genome per ml is provided in Merten et al. This greater ratio demonstrates that some vectors are degraded during the production phase at 37° C. and that serum contents enhance this vector degradation. This difference highlights that serum and time of harvest are key points to starting the concentration and purification steps with a convenient batch exhibiting a ratio PP/TU less than 900:1. In a preferred embodiment of the invention, the first harvest time is between 24 h and 36 h post transfection. Any subsequent harvest may be done 12 h after the preceding harvest. Crude batches with a higher ratio do not lead to the required final product after the concentration and purification steps.

Compositions containing the vectors described in the prior art contain contaminants, which can have a harmful influence on target cell phenotype and can affect the capacity of the target cells, transduced by retroviral vectors preparations, to express or highly express the transgene of interest. Changes in such phenotypes can occur after transduction and cell proliferation or cell viability can be affected in transduced cells. The present invention provides several robust and scalable purification processes allowing for a remarkable decrease in contaminating protein and DNA concentrations and in physical to infectious particles ratio compatible with delicate refractory target cells and in vivo preclinical trial requirements.

EXAMPLES

The examples below are provided to help better understanding the invention although the invention is not limited to these examples.

Material and Methods

Plasmid Construction.
Three vectors were used in order to produce a recombinant virion or recombinant retrovirus. A first vector provides a nucleic acid encoding a viral gag and pol genes (FIG. 2A). These sequences encode a group specific antigen and reverse transcriptase, (and integrase and protease-enzymes necessary for maturation and reverse transcription), respectively, as discussed above. A second vector provides a nucleic acid encoding a viral envelope (env) (FIG. 2B). A third vector provides the cis-acting viral sequences necessary for the viral life cycle (FIG. 2C). This third vector also contains a cloning site for a heterologous nucleic acid sequence to be transferred to a target cell. A schematic illustration of a suitable vector is shown in FIG. 2C with the GFP as a transgene but which can be replaced by any gene or sequence of interest such shRNA or miRNA.

Viral Vectors Manufacturing Processes. Cell Lines and Culture Conditions.

Viral vectors were produced using Human Embryonic Kidney (HEK293T) cell line. Human colon carcinoma (HCT116; ATCC No CCL-247) adherent cell line is used for quantification of infectious particles. All cells were provided by the American Type Culture Collection (ATCC) and cultured in Dulbecco's Modified Eagle's Medium (DMEM, Gibco, Paisley, UK) supplemented with 10% FCS; 1% penicillin/streptomycin and 1% ultraglutamine (PAA) at 37° C. in a humidified atmosphere of 5% $CO_2$ in air. For the production of viral vectors supernatants DMEM was only supplemented with 1% penicillin/streptomycin and 1% ultraglutamine (PAA).

Viral Vectors Production.

Viral vector production was performed in a 10-layer CellSTACK (6320 $cm^2$, Corning). HEK293T cells were seeded at $9.5 \times 10^3$ viable cells/$cm^2$ in DMEM supplemented with 10% FCS; 1% penicillin/streptomycin and 1% ultraglutamine (PAA) and placed at 37° C. in a humidified atmosphere of 5% $CO_2$ in air. Four days after seeding, the supernatant was discarded and replaced by fresh DMEM without FCS supplemented with 1% penicillin/streptomycin and 1% ultraglutamine (PAA) before transfecting the cells.

The tri-transfection mix was composed by the following three plasmids: pENV, pGagPol, pLV-EF1-GFP. The final concentration was adjusted to 40 mg/ml-1 using sterile water. $CaCl_2$ (2.5M) was then dripped to the plasmid-water mixture under soft checking to reach a final concentration of 500 mM. The obtained mixture was then dripped to an equivalent volume of Hepes Buffered Saline (HBS 2×) and incubated at room temperature for 20 minutes. After incubation, the transfection mixture was added to the cell culture media and incubated for 24 hours at 37° C. in a humidified atmosphere of 5% $CO_2$ in air.

24 hours post-transfection, the supernatant was discarded and replaced by fresh non-supplemented DMEM and the cells were incubated at 37° C. in a humidified atmosphere of 5% $CO_2$ in air. After medium exchange, the supernatant was collected several times (32 h, 48 h, 56 h and 72 h post transfection). Some fresh and no supplemented media were added and the cells were incubated prior to further harvests at 37° C. in a humidified atmosphere of 5% $CO_2$.

Each harvest was clarified by centrifugation for 5 min. at 3000 g before being microfiltered through 0.45 µm pore size sterile filter unit (Stericup, Millipore). The whole set of harvest were then pooled to supply the crude harvest.

LDH Cytotoxicity Assay.

LDH cytotoxicity assay kit II (PromoKine) was also used to measure the LDH enzyme (Lactate Dehydrogenase) released from the 293T producer cells after transfection by the plasmids encoding lentivectors particles. The 293T cell's supernatant was used as "Low control" meanwhile, 293T cells were lysed by the cell lysis solution in order to represent "the high level control". Then, the LDH assay was performed as per the manufacturer protocol on each crude supernatant recovery as sample to assess the 293T cells mortality during the different lentivectors production processes. LDH Cytotoxicity Assay Kit-II utilizes the WST reagent (Water Soluble Tetrazolium) for detection of LDH released from the damaged cells. The assay uses an enzyme coupling reaction; LDH oxidizes lactate to generate NADH, which then reacts with WST to generate a yellow color. LDH activity was then quantified with a spectrophotometer (Glomax MultiDetection System, Promega reference) at 450 nm optical density. The assay was repeated in simplicate for each tested crude supernatant.

Viral Vectors Concentration and Purification.

The concentration and purification of the crude harvest was first performed by tangential flow ultrafiltration using polysulfone hollow-fiber cartridges. The supernatant was then diafiltered for 20 diavolumes in a continuous mode diafiltration against DMEM or TSSM buffer. Once the diafiltration performed, the retentate was recovered and further concentrated on ultrafiltration disposable units.

The hollow fiber filtration (HFF) retentate was then benzonase treated by addition of Benzonase (250 U/µl)) for a final concentration of (72 U/ml), and $MgCl_2$ (1.0 mM) for a final concentration of 1 µM, before being incubating at 37° C. for 20 minutes.

The post HFF material was then further purified by ion exchange chromatography (IEX) on Sartobind Q75 (Sartorius) disposable membrane using an AKTA purifier system (GE Healthcare). The ion exchange membrane was equilibrated with 5 column volumes of non-supplemented DMEM (or TSSM) at 2 ml/min. The viral supernatant was then loaded on the membrane at 2 ml/min using a sampling loop. The flow through was collected. The following step gradient was applied to the AKTA system: 0M, 0.5M, 1.2M and 2M NaCl. The elution pic (collected with the 1.2M NaCl step gradient) was immediately 10× diluted in the following buffer: 20 mM Tris+1.0% w/v Sucrose+1.0% w/v Mannitol, pH7.3 and further concentrated on ultrafiltration disposable units.

Functional particle quantification using qPCR. Transduction unit titration assays were performed as follows. HCT116 cells are seeded in 96-wells plate at 12500 cells per well and 250 µL of DMEM supplemented with 10% FCS; 1% penicillin/streptomycin and 1% ultraglutamine (complete medium). 24 h later, five serial dilutions are performed with complete medium for each vector sample and a rLV-EF1-GFP internal standard. The cells are transduced by these serial dilutions in the presence of 8 µg/mL POLYBRENE® (Sigma). For each sample series, one well of non-transduced cells is added for control. Three days post-transduction, cells are trypsinized and each cell pellet is taken up with 250 µL of PBS. 100 µL of the cell suspension are then placed in a cuvette and the fluorescence intensity is measured using the Versafluor (Biorad) in RFU (relative fluorescence unit). The titre is determined by transducing units/ml (TU/mL) using the internal standard whose titre was previously determined by FACS.

Physical Particle Quantitation by p24 ELISA Assay.

The p24 core antigen is detected directly on the viral supernatant with a HIV-1 p24 ELISA kit provided by Perkin Elmer. The kit is used as specified by the supplier. The captured antigen is complexed with biotinylated polyclonal antibody to HIV-1 p24, followed by a streptavidin-HRP (horseradish peroxidase) conjugate. The resulting complex is detected by incubation with ortho-phenylenediamine-HCl (OPD) which produces a yellow color that is directly proportional to the amount of p24 captured. The absorbance of each microplate well is determined using microplate reader and calibrated against absorbance of an HIV-1 p24 antigen standard curve. The viral titer expressed in physical particles per ml is calculated from the amount of p24 knowing that 1 pg of p24 corresponds to $10^4$ physical particles.

Residual DNA Quantification.

The residual amount of DNA in each sample was determined using Quant-iT kit PicoGreen dsDNA reagent and kits (Life Technologies) as specified by the supplier. A calibration curve is performed using a plasmid diluted in sample dilution buffer (DMEM or TSSM). The reaction itself consists of mixing 25 µl of the sample with 25 µl of TE buffer and 50 µl of the working solution of PicoGreen® dye in a 96-well plate. The reaction is then incubated in the dark for 5 minutes to permit the dye to bind to double stranded DNA. The fluorescence of the samples is then measured on a plate reader at excitation/emission of 435/535 nm.

Total Protein Quantitation.

The total amount of protein in each sample was determined using the DCTM protein kit (Biorad) whose method derives from the method of Lowry. The kit is used as specified by the supplier. A calibration curve is performed using BSA diluted in sample dilution buffer (DMEM or TSSM). The assay is based on the reaction of protein with an alkaline copper tartrate solution and Folin reagent. As with the Lowry assay, there are two steps which lead to color development: The reaction between protein and copper in an alkaline medium, and the subsequent reduction of Folin reagent by the copper-treated protein.

SDS-PAGE Gel Electrophoresis.

The samples are denatured 5 min at 95° C. in "Sample Buffer 4×" (Biorad) and "Reducing Agent 20×" (Biorad). After denaturation, samples are placed in the wells of a "Criterion XT Bis-Tris 4-12% gel" (Biorad). The molecular weight marker "Precision Plus Protein Dual Color Standard" is placed beside the samples. The migration is performed in the "XT MOPS buffer" (Biorad). After migration, the gel is rinsed several times with water before being stained with the "Biosafe Coomassie Stain" (Biorad). Eventually, several water rinses are performed to obtain the desired contrast.

Cell Transduction. Cell Culture.

Human lung embryonic fibroblast cell lines (IMR90) were obtained from the American Type Culture Collection (No CCL-186) and cultured in Dulbecco Modified Eagle Medium (DMEM; Gibco, Carlsbad, Calif., USA) supplemented with 10% fetal bovine serum (FCS; Gibco) at 37° C. in a humidified atmosphere incubator containing 5% $CO_2$.

Transduction of IMR90 Cells Using Viral Vectors.

IMR90 cells are seeded in 6-wells plates at 50000 cells/well 24 hours before transduction. Cells were then transduced with TU normalized eGFP carrying lentiviral vectors at different M.O.I. going from 5 to 200. The transduction supernatant is removed after 5 hours. At 6 days post transduction cells were harvested and eGFP expression was analyzed by flow cytometry.

Cell Proliferation Assay.

Cell proliferation was measured using 3-(4,5-dimethylthiazol-2-yl)-2,5-diphenyltetrazolium bromide (MTT; Sigma) colorimetric dye reduction method. IMR90 cells were seeded in a 96-well plate at a density of $1.5 \times 10^3$ cells per well in DMEM containing 10% FCS. The cells were cultured for 24 hours prior to transduction using viral vectors at different purification level at M.O.I. 40 and 150 for each viral vector. Five or fourteen days post-transduction 20 µl of 3-(4,5-dimethylthiazol-2-yl)-2,5-diphenyltetrazolium bromide (MTT; 5 mg/ml; Sigma) in phosphate buffered saline (PBS) were added to each well and cultured for another 2.5 hours at 37° C. Then the culture media was discarded and the dark blue crystals were dissolved in 100 µl dimethylsulfoxide (DMSO) into each well. The wells were then homogenized before measuring the optical density (OD) at 560 nm using a spectrophotometric plate reader (Glomax MultiDetection System, Promega). Proliferation assays were repeated in triplicate for each tested viral vectors.

LDH Cytotoxicity Assay.

LDH cytotoxicity assay kit II (PromoKine) was used to measure the LDH enzyme (Lactate Dehydrogenase) released from the cells after transduction. Human fibroblast cells were seeded in a 96-well plate at a density of $1.5 \times 10^3$ cells per well in DMEM containing 10% FCS and then serum restricted to 2% FCS for 24 h. The cells were then transduced using viral vectors at different purification level at M.O.I. 40 and 150 for each viral vector. Six days post transduction the LDH assay was performed as per the manufacturer protocol. LDH Cytotoxicity Assay Kit-II utilizes the WST reagent (Water Soluble Tetrazolium) for detection of LDH released from the damaged cells. The assay uses an enzyme coupling reaction; LDH oxidizes lactate to generate NADH, which then reacts with WST to generate a yellow color. LDH activity was then quantified with a spectrophotometer (Glomax MultiDetection System, Promega reference) at 450 nm optical density. The assay was repeated in triplicate for each tested viral vectors.

Empty Cassette Vector Production for Microarray Analyses.

An empty cassette carrying lentiviral vector (rLV-EF1) without cDNA, was produced at different purities for microarray studies. Batches B and C of rLV-EF1 vectors were purified from the same crude harvest. An additional production was achieved in the presence of 10% Fetal Bovine Serum (BIOWEST) in order to generate a B batch, hereinafter mentioned as B-S batch.

Culture of Foreskin Cells.

Human foreskin fibroblast cells were obtained from the American Type Culture Collection (No CRL-2097) and cultured in EMEM (Earl's Minimum Essential Medium, GIBCO) supplemented with 10% Fetal Bovine Serum (BIOWEST), 1% penicillin/streptomycin (PAA) and 2 mM glutamine (PAA). Cells were maintained at 37° C. in the presence of 5% $CO_2$ and passaged twice a week at 5000 cells/$cm^2$. The present invention is not limited to primary cells, such as human foreskin fibroblast cells.

Transduction of foreskin cells for transcriptomics analysis. Human foreskin fibroblasts were seeded at 5000 cells/$cm^2$ in T25-flasks 24 hours before transduction. Cells were transduced in quadruplicate at M.O.I 40 and 150 using the batches B, C and B-S of rLV-EF1 vector in a final volume of 5 mL and in the presence of 4 µg/mL of POLYBRENE® (Sigma). A non-transduced control only received 4 µg/mL of POLYBRENE®. The transduction supernatant is removed after approximately 16 h. Cells were trypsinized 54 hours post-transduction, washed with 1×PBS, centrifuged and the pellets were kept at −80° C. Pictures were taken 48 hours post-transduction.

RNA Extractions.

Total RNA samples were extracted from cell pellets using the TRIZol® Plus RNA Purification System (Life Technologies) according to manufacturer's instructions. Total RNA concentration and purity were determined using a Nanodrop 1000 spectrophotometer (Nanodrop Technologies). RNA quality and integrity were checked with the Agilent 2100 Bioanalyzer (Agilent Technologies, USA) and were conform to Agilent microarrays' requirements.

DNA Microarray Experiments.

Microarray experiments were performed at the Biochips Platform of Genopole, University of Toulouse, INSA, UPS, INP, CNRS & INRA (Toulouse, France) according to manufacturer protocols. Briefly, after addition of a dilution of exogenous RNA from the one color RNA Spike-In Kit (Agilent Technologies) for quality control check, 100 ng of total RNA were converted to cRNA, amplified and cyanine 3-labeled using the Agilent Low Input Quick Amp kit. 1650 ng of cyanine 3-labeled cRNA were hybridized at 65° C. for 17 hours at 10 rpm to Agilent Whole Human Genome Oligo Microarrays 4×44K version 2, containing 44,000 probes targeting 27,958 genes. Hybridized arrays were washed and scanned on the Agilent high-resolution scanner G2505C and the images were analyzed using Feature Extraction 10.10 (Agilent Technologies). After quality control based on Feature Extraction QC reports, 3 or 4 replicates were retained per condition.

Microarray Data Statistical Analyses.

Raw datasets from Feature Extraction were imported into GENESPRING® GX 12 Software (Agilent Technologies) and normalized using the 75th percentile methods. Probes were then filtered by flag values attributed by GENESPRING® when importing Feature Extraction data (for each probe, one of the following flag is affected: "detected", "not detected" or "compromised"). Probes detected and not compromised in more than 60% of replicates in at least one condition were retained (eliminating undetected or compromised spots). Baseline transformation of intensity values to median of all samples was applied for profile plot representations. It means that, for each probe, the median of the log summarized values from all the samples is calculated and subtracted from each of the samples. In order to identify differentially expressed probes between each condition and the control condition, independent t-tests were performed with Benjamini-Hochberg multiple test correction and a corrected p-value <0.05. Probes with absolute value of fold changes (FC) ≥1.5 were retained as differentially expressed for both up and down-regulated probes. Probes having absolute value of fold changes <1.3 were considered as non-differential.

Results

Cell Transduction Efficiency on Different Cell Types.

When stable gene over expression or silencing is required, the first assay to perform is the choice of the required multiplicity of infection (M.O.I.) to obtain the optimal gene modulation. All cells do not exhibit the same permissivity to retroviral or lentiviral vectors. Target cells are transduced with increasing quantities of GFP expressing lentiviral vectors to determine the conditions in which cells are completely transduced and to identify the corresponding gene expression level. In FIGS. 3A and 3B, it was observed that as the M.O.I. increases, first the number of transduced cells rises to 95-100% of the target cells and secondly the level of GFP expression is enhanced. This phenomenon is observed in immortalized cell lines, in primary cells and in stem cells. This result shows a dose-effect of gene delivery with lentiviral vector for all cells tested but also that the M.O.I. used for a cell type is not transposable to another cell type. Each cell type requires a specific M.O.I.

Lentiviral Vector Titer Quantification.

Titers of viruses in general, and lentiviral based vectors in particular, depend on the method and cells used for titration. The quantification of vector particles capable of achieving the steps of the transduction pathway from cell entry to gene integration and gene expression depends on the vector itself and cell characteristics.

Concerning the cells used for vector titration, it is important to ensure that as shown in FIGS. 3A and 3B, the target cells are readily permissive, as it was demonstrated that the permissivity of all the cell types are not equivalent. Another point is that the transduction efficiency must be easily monitored for reliable quantification for any transgenes and vectors over time. Here, in each titration experiment a standard GFP expressing lentiviral vector is quantified in terms of efficient units both by FACS (represented by the number of Transducing Units per ml TU/ml) and qPCR (represented by the number of Integrated Genome per ml IG/ml) after HCT116 transduction with serial dilutions of the vectors according to the material and methods as set forth above. Both results give a relative number of efficient particles for transduction but their respective absolute numbers do not give the same titer depending on the PCR itself and the target sequence used for amplification. These data show that it is difficult to compare precisely these different approaches based on the functional titers in the absence of standardized methods that should include a reference batch with a known titer and a define target cell type.

In parallel, the determination of total particles is quantified with the P24 Elisa kit to estimate the total vector particles, even those that do not contain any genomic RNA and/or that are devoid of envelope proteins. Both titers are useful to determine the ratio between the physical particles PP that reflect the total particles and the biological titer that gives the real transduction ability. This ratio gives an estimation of the vector purity and integrity. Another ratio is used to reflect the vector integrity or infectivity and is expressed as the number of IG per ng P24 (1 ng of P24 corresponds to $10^7$ PP).

Viral Vectors Production Process.

Retroviral and lentiviral based-vectors, according to the invention, are produced by tri-transfection into 293T cells using standard calcium phosphate procedures. 24 hours after transfection (Sena-esteves et al., 2004), cells are washed with medium without serum and viral supernatants are collected 24 hours later and filtered. Vectors in the prior art are commonly produced in serum-containing medium and concentrated by ultracentrifugation or centrifugation on central units provided by different suppliers. In the present invention, the crude batch referred to as batch A in FIG. 5A, exhibits an average titer of about $10^6$ TU/ml dependent on the expression plasmid constructs. After the concentration steps described herein the titer reaches up to $10^7$-$10^8$ TU/ml, for example. These small-scale batches produced by these standard methods exhibit several drawbacks. First, the scale-up is difficult due the restricted capacity of these simple methods. Secondly, the methods are restricted to concentration and do not permit a significant removal of the medium content. To avoid the presence of proteins and elements of the serum, the process according to the invention, harvests the vector supernatants in a serum free medium before submitting batch A to ultrafiltration and/or chromatography to concentrate and purify the vector batch. This is important as in some instances, the vectors need to be used at high M.O.I. in vitro and in vivo, especially for non-integrative lentiviral vectors (FIGS. 10A and 10B).

Serum Influence on Vector Titer.

The present invention provides an optimized robust process for the production of high titer viral supernatants in serum free medium. Lentiviral vectors rLV-EF1-GFP were produced by transient tri-transfection in 293T cells, in 0, 5 and 10% FCS (Fetal Calf Serum) by using standard phosphate calcium procedures. EF1 alpha (human elongation factor 1 alpha) promoter is an ubiquitous strong promoter. Viral supernatants were harvested and 15 μg of total proteins were loaded on a SDS-Page gel to analyze the total protein contents. Results show that the crude supernatant produced without serum contains a lower quantity of proteins directly linked to the absence of serum. In parallel, the ratio between PP and TU was determined with and without serum. It was demonstrated that titers (TU/mL) and the PP/TU ratio remained stable in all conditions. To conclude, producing retroviral vectors without serum does not decreases the vector production efficiency (FIG. 4C) but decreases the total protein content of the sample (FIG. 4B and Table 1).

Sequential Harvesting of Vector Particles Following the Cell Transfection.

The present invention describes the comparison of the induced toxicity on transfected producer cells depending on the induction of sodium butyrate (at 18 hours post-transfection) or not and the number of harvests during the 72 h post transfection. These experiments show that the functional titre is higher than $10^6$ TU/ml in any crude supernatant harvest and highlight the strong impact of the number of supernatant harvests and sodium butyrate induction on the resulting toxicity of producer cells. In one hand, applicants notice that the number of recoveries (See FIG. 11B) and induction or not with sodium butyrate has a small impact on crude supernatant's titre with an improved production of transduction units (see Table 3, TU/production) by a factor of two for viral vector production without sodium butyrate induction, harvested by five steps. On the other hand, the concentration of total DNA released in the crude supernatant produced in absence of sodium butyrate induction and serum, harvested by multiple steps adjusted to half life of the vector particles, is the lowest, with a factor of seven compared to a production with sodium butyrate induction and harvests times fixed at 64 h and 88 h post-transfection. These results are confirmed by LDH Cytotoxicity assays made directly on crude supernatant and show that transfected cells lysis is limited when the crude supernatant is produced in absence of sodium butyrate induction and serum, harvested by multiple steps adjusted to half life of the vector particles. At the same time, the concentration of total DNA in the crude supernatant and cytotoxicity levels are increased by sodium butyrate induction and harvests times fixed at 64 h and 88 h post-transfection showing that cell lysis is enhanced in these production conditions. When the crude supernatant is harvested without sodium butyrate induction by only two steps at 40 hours and 64 hours following cell washing, the induced toxicity reaches 82% and 48% although with intermediate harvests the toxicity on transfected cells does not exceed 30% with an average of 13.3% for the first three harvests and 16.4% for the last harvest (Table 3). Thus, the recovery of crude supernatant realized by multiple steps, comprised between 3 and 6, at regular interval is the starting point to obtain the claimed purified RNA based viral vector composition. The different harvests are performed at specific times post transfection in relation with the half life of the vector particles at 37° C. which is about 8 hours depending of the producer cell type and the culture medium (Le Doux et al., 1999). The harvesting by multiple steps related to the vector half life, without sodium butyrate induction and serum are the best conditions to produce a crude supernatant, i.e Batch A according to the present invention. These results highlight that the initial crude supernatant composition is largely influenced by the production process itself and this starting composition has a dramatic impact on the target transduced cells in terms of toxicity.

Vector Concentration and Purification.

The methods according to the invention include two types of concentration and/or purification batches (C and D) associated with a serum free production process (corresponding to the obtaining of batch A). These methods were compared with a standard and commonly used concentration process based on either ultracentrifugation or centrifugation on central units (corresponding to the obtaining of batch B). The different batches correspond to different purification strategies going from no purification to several purification steps based on ultrafiltration and chromatography. The four purification processes have an increasing quality in terms of contaminant removal (FIGS. 6 and 7).

Process a Corresponding to the Obtaining Batch A:

This type of batch does not include any purification step and corresponds to the post-clarification harvest. This type of batch usually exhibits one or more of the following features: (i) an average final titer at about $10^6$ TU/ml, dependent on the expression plasmid constructs (Table 1); an average final DNA contaminants concentration up to 650 ng/ml; (iii) an average final protein contaminants concentration up to 200 μg/ml; and (iv) an average final PP/TU ratio comprised between 500 and 900 (Tables 1 and 2) or less.

The viral vectors produced using this process are suitable for transducing some permissive immortalized cell lines when the required working M.O.I. can be low. This batch is used as reference in the contaminants removal characterization studies of the others batches (i.e. the contaminants of this batch represent 100% of the production process impurities) (Table 1 and FIG. 6). All the following data are related to this reference crude batch. Batch A is an optimized batch because of the absence of serum and sodium butyrate induction and the choice of different harvests times based on half life specific to the viral particle.

Process B Corresponding to the Obtaining of Batch B.

This process corresponds to the post clarification harvest (serum-free culture medium) having undergone a concentration step by ultrafiltration using centrifugation ready-to-use units. This concentrated batch results from the same process as that described in FIG. 4A but without serum. This type of batch usually exhibits one or more of the following features: (i) final vector titers between $1\times10^7$-$1\times10^8$ TU/ml; (ii) a process recovery of efficient vectors according to the invention, at about 47% compared to the batch A; (iii) a concentration factor of 95 compared to batch A (Table 2); (iv) a DNA removal at about 71% of initial contaminants compared to the batch A; (v) a protein removal at about 56% of initial contaminants (FIG. 6) compared to the batch A; and (vi) an average final PP/TU ratio at about 500 or more (FIG. 8). This ratio increases compared to those obtained for the crude batch showing that these concentration methods damaged the viral particles during the process itself even without serum. This phenomenon is amplified in the presence of serum.

This product is advantageously produced compared to previously published virus-based vectors with a serum containing crude batch. It exhibits the same characteristics of the ones described in the literature using ultracentrifugation (FIG. 5B). The advantages of such a process is to concentrate the retroviral vectors particles when higher titers than the ones provided by the process A are required for transducing cells. This process is based either on the concentration of the crude harvest using an ultrafiltration technique based centrifugation ready-to-use units or on ultracentrifugation. Both products produced without serum in the crude supernatant exhibit the same protein profile after loading on a SDS page gel (FIG. 5B). With fetal calf serum (FCS) for example, the protein profile of vectors concentrated with such technique is shown in FIG. 4B and reveal a smear of bands in which the specific viral proteins are indistinguishable by either their size or by their low intensity. This result prompted us to use this process B of concentration on vector batches produced without serum to be able to compare the consequences of downstream concentration and purification methods on the vector particles themselves independently of the presence of serum.

For the centrifugation on central units, the mode of operation is by usual flow filtration using centrifugal forces for pressure set up. Thus, such a technique does not allow the pressure monitoring which is a critical point for vectors integrity and viability. The type of membrane used in this technology increases non specific adsorptions compared to other type of membrane. Therefore, not only the vectors but the impurities are also concentrated. In fact, a low purification level (respectively between 1 and 3 and between 1 and 2 for DNA and proteins) (See, FIG. 9 as an example) is reached. In parallel, this process is quite damaging for biologically active retroviral vectors as shown by the PP/TU ratio increasing from the process A (between 200 and 350 in the experiments of FIG. 8) to the process B (up to 650 in the experiments of FIG. 8). Despite such an increase in the PP/TU ratio, these state of the art processes based on ultracentrifugation or ultrafiltration on central units are largely used in the literature. This process B is suitable for transducing immortalized cell lines when the required working M.O.I. needs to be high but is not adapted for transducing fragile and primary or stem cells that may submit differentiation or reprogramming processes with functional phenotypic requirements.

Here, it was considered that performing ultrafiltration without controlled operating conditions based on the ionic strength, pH and pressure would not allow an efficient separation even for proteins which differ in size by less one order of magnitude. This last point is crucial and highlights that an ideal ultra-filtration step will not only concentrate vector particles but also purify them by removing contaminants such as host cell proteins and DNA since the large size of lentiviral vectors (120 nm). Thus, the following process called C has been developed to increase the titer of batch A while preserving the quality and purity of the batch.

Process C Corresponding to the Obtaining of Batch C.

This process corresponds to the post clarification harvest (serum-free culture medium) having undergone a concentration and diafiltration step by ultrafiltration using hollow fibers. This type of batch usually exhibits one or more of the following features: (i) a final titer between $1 \times 10^7$-$1 \times 10^8$ TU/ml; (ii) a process recovery of efficient vectors according to the invention at about 69% compared to batch A; (iii) a concentration factor of about 25 and but typically between 20 to 40. (Tables 2 and 3); (iv) a DNA removal at about 82% of initial contaminants compared to the batch A (from 70% to 90%); (v) a protein removal up to 98% of initial contaminants compared to the batch A (FIG. 9); and (vi) an average final PP/TU ratio between 200 and 600 (FIG. 8).

Here, the ratio PP/TU remains stable between the batches A and C showing that the process to obtain the batch C does not damaged the viral particles as it did for the batch resulting from process B corresponding to the obtained batch B (FIG. 8).

The advantages of such a process are to combine the concentration and the purification of the retroviral vectors particles from the clarified crude harvest. The technique is less damaging for the retroviral vectors than the concentration technique used for batch B. Ultrafiltration technology used in the process to obtain batch C is very different from that used to obtain the batch B. In fact, the approach used in the process to obtain batch C is based on the concentration of the crude harvest using ultrafiltration technique using hollow fibers. The mode of operation of this technique is by tangential flow filtration using pump forces for pressure set up. Such a technique allows monitoring and adapting the pressure for maintaining the vectors integrity and viability, according to the teachings of one skill in the art. For example, inlet flux vector supernatant must be maintained at a low level and the transmembrane pressure must be low and completely stable during all the process. The type of membrane used in this technology does not increase non-specific adsorptions compared to the one used for process to obtain batch B. Therefore, this softer process allows high vector recovery associated with high impurities removal. Moreover, the low shear stress achieved using this technique, permits one to decrease the PP/TU ratio, at about 300 or below (see, FIG. 8 as an example), from the one obtained for the clarified crude harvest (batch A). This less damaging technique allows the strong removal of most of the impurities (respectively, 82% and 98% of initials DNA and protein contaminants compared to the batch A) and permits one to increase the purification level from 1.7 to 4 and from 1.1 to 32 respectively for DNA and proteins, compared to batch B (FIG. 9). Therefore, the good compromise between recovery, impurities removal and a beneficial concentration factor (20) make the retroviral vectors produced by this process the ideal tool to transduce delicate cells like primary or stem cells even when high working M.O.I. are needed.

Process D Corresponding to the Obtaining of Batch D.

This process to obtain the batch D comprises the steps of the process used to obtain the batch C enhanced by a concentration step then optionally enriched by ultrafiltration using centrifugation ready-to-use units, a benzonase treatment and a chromatography based purification. This type of batch usually exhibits one or more of the following features: (i) a final titer between $1 \times 10^7$-$1 \times 10^8$ TU/ml; (ii) a process recovery (purified virus DNA vector according to the invention) at about 12% compared to batch A; (iii) a concentration factor of about 7 (between 5 to 10) (Table 2); (iv) a DNA removal at about 98.8% of initial contaminants compared to the batch A (from 80 to 99%), (v) a protein removal at about 99.9% of initial contaminants compared to the batch A (from 80 to 99%), (FIG. 6); and (vi) an average final PP/TU ratio between 100 and 400 (FIG. 8).

The advantage of such a process D is to reach the requirements for in vivo injections with a protein removal at least 90% and up to 99.9% and a DNA removal at least 90% and up to 99.9% 98.7% of initial contaminants (FIG. 6). The IEX (Ion Exchange) chromatography step allows the separation between biologically active and non-active particles to reach the lowest PP/TU ratio so far described of less than 300 (See, FIG. 8 as an example). This high purification oriented process allows one to increase the purification level from 20-40 to 120-160 for proteins (See, FIG. 9 as an example). This process shows the highest specific activities of all the processes described herein, meaning that the removal of the impurities is the most efficient using this purification method (See, FIG. 7 as an example). The retroviral vectors produced according to the process D are therefore suitable for in vivo injection into mammals or animals.

An additional centrifugation using ready to use units (as used in process B) may be added at the end of C and D processes to increase the final titer. However, this extra concentration step can lead to an increase in the PP/TU ratio as the ready to use centrifugation unit are damaging for the vectors because of the non-specific adsorption to the support due to the chemical nature of the unit.

As described herein, retroviral vectors have been produced according to the processes used to obtain batches A to D. The batch preparations have been compared to evaluate the consequences of transduction on cells toxicity, viability and proliferation. Such comparisons are important if the retroviral vectors are to be used for transduction of immortalized cell lines or for in vivo animal injection (Table 2 and FIGS. 6-9).

Cell Transduction with Vectors that Exhibit Different Levels of Concentration and or Purity.

Even if lentiviral vectors are the most efficient means of delivering a gene or a shRNA into animal or mammalian cells, several issues remain as barriers for use of such vectors, including gene delivery reproducibility, cell viability or toxicity, dose effect monitoring or homogeneity between results obtained in immortalized, primary and stem cells. In fact, as described in FIG. 3, gene transfer efficiency requires specific development to determine the adapted M.O.I. regarding the objectives of the experiment and the target cells. Some cells (U937, primary lymphocytes, hematopoietic stem cells, THP1) require higher M.O.I. than others (293T, DA0Y, HCT116). Very often, primary cells are less permissive than immortalized cells but some established cells like THP1, Jurkat or U937 do need a M.O.I. higher than 50. These M.O.I.s are deemed difficult to apply due to an induced toxicity of lentiviral vectors (Yamada et al, 2003). Transduction with non-integrative lentiviral vectors (NILV) highlights this issue due to the fact that they require high M.O.I. to efficiently transduce target cells as shown in FIG. 10. In fact, NILV vectors require a M.O.I. of 40 to transduce 63% of target cells although ILV transduces 100% of target cells at M.O.I. 10. Moreover, a M.O.I. of 150 must be used with NILV to reach the same level of expression than with ILV at M.O.I. 5. Efficient transduction of human or animal hematopoietic stem cells also requires high M.O.I. in order to re-implant then into human or animals for gene therapy or animal models development. Primary cells also need to be transduced at high M.O.I. to express target genes at a convenient level to reverse a phenotype or a disease. The aim of this invention is to find the optimal balance between a level of expression in target cells and the resulting cell viability. As demonstrated herein, reducing the protein and DNA contents in the concentrated vector supernatant is a way to protect cells against cell arrest and mortality. This is also an important consideration for cell reprogramming into iPS with ILV and NILV to avoid the interference of contaminants in the reprogramming process.

The present invention provides solutions to these problems and brings complementary information about this apparent toxicity. Lentiviral vectors have been produced with different grades of concentration with an additional purification step or not. Vector concentration has been reached according to the different approaches used based on either commonly used technologies (based on ultracentrifugation or concentration using central units illustrated in FIG. 4A or tangential flow filtration illustrated in FIG. 5A). Ultracentrifugation or centrifugation in central units concentrates lentiviral vectors but also cellular debris, membrane fragments, and proteins derived from culture media of virus-producing cells. The data described below show that both concentrated batches B and C lead to a same transduction efficiency but induce very different cell phenotype consequences.

Crude Vector Composition.

When 293T cells are tri-transfected to produce recombinant retroviral or lentiviral vectors in the absence of serum, these cells stop growing and may secrete in the supernatant stress proteins and toxic elements. FIG. 11A shows that virus-producing cells exhibit a high production rate of LDH after tri-transfection. This result highlights the presence in culture medium of toxic proteins secreted by the producer cell line during vector production. This unwanted material in the crude preparation, but also in the concentrated batch, may induce cell perturbations when used to transduce target cells especially in delicate primary cells and may cause immunogenic reactions in experimental animal models after in vivo administration. This crude vector composition is clearly impacted both by the number and the time of vector harvest post transfection as shown in Table 3. The LDH effect of the vector harvest is increased when vector supernatants are harvested on a 24 h interval without considering the vector half life. The LDH effect is lower than 30% when, for example, four harvests are repeated on a 12-16 h intervals as described in Table 3, but reaches respectively 80% and 48% when the vector harvests are repeated on a 24 h interval. Thus, the recovery of crude supernatant performed by multiple collection steps, comprising between 3 and 6 collections, at specific intervals provides a method for obtaining a purified RNA based viral vector composition i.e a recovered crude supernatant. The multiple collection steps are chosen at specific times post transfection depending on the half life of the vector particles at 37° C., which is about 8 hours, depending of the producer cell type and the culture medium (Le Doux et al., 1999). Thus, in addition to the absence of serum during vector production, this second parameter based on time and number of harvests during vector production allows one to produce a crude starting material of high quality which minimizes not only the protein concentration but also the cytotoxicity. Here, it is demonstrated that a combination of steps summarized in the FIG. 5A is able to reduce undesirable effects in target cells. This process includes serum free medium, sequential harvesting and ultrafiltration.

Purity Effect on Cell Transduction Efficiency.

Vector transduction effects on primary cells, foreskin cells (ATCC-CRL-2097), several days after transduction was investigated. The four batches described above referred to as batches A, B, C and D were produced and used to transduced target cells at medium and high M.O.I. respectively 40 and 150 to evaluate a gradual effect of the vector itself and the vector environment. First, the cells were checked to determine whether they can express the reporter gene GFP and the results of GFP expression with the different batches are demonstrated in FIGS. 12A and 12B respectively five and eleven days after transduction. These data show that all transduced cells express at high level the GFP reporter gene with all the batches. Then, the GFP expression level seems to be independent of the purification grade. Once a vector enters into a viable target cells, the transduction pathways are not restricted and transgene expression is efficient. In parallel, these pictures show that the cell numbers in all the wells are very different even if the same number of cells were plated two days before transduction.

Purity Effect on Cell Proliferation and Viability.

Six and eleven days after transduction, transduced cells with all the vector types were observed. The same experiments were performed on foreskin cells at M.O.I. 40 and 150 to evaluate the resulting cell quantities in each condition. As presented in FIG. 13, an effect of vector purity on the cell viability was seen since the number of cells transduced with the B batch represent only 6% of the number of cells transduced with the C batch in the same conditions. This result was confirmed by using a colorimetric MTT assay to assess the viability and the proliferation rate of target cells after transduction. FIG. 14A shows that transduction of cells with B batch induces a growth retardation proportional to the M.O.I. used. A growth arrest of 40% and 70% is respectively observed at M.O.I. 40 and 150. This growth arrest may explain the low quantity of cells following transduction with the B batch observed before. In fact, after 11 days of cell culture after transducing including one passage, results show that the number of cells is affected in a large proportion with the B batch at both M.O.I. 40 and 150 although at M.O.I. 40, the cell quantity is stable when cells are transduced with the C or D batch. At higher M.O.I., the cell quantity is affected to a lesser extent than with the B batch. No significant difference was observed between the C and D batches suggesting that the purification level reached after the ultrafiltration is sufficient to protect cells against a cell growth arrest for in vitro experiments. In the FIGS. 14B and 14C, the proliferation rate of transduced cells with A, B, C and D batches was determined and it was confirmed that the C batch protects cells against the growth arrest previously observed. Transduction of cells with a batch B-S shows an amplified cell arrest compared as those obtained when cells are transduced with a B batch highlighting that the combination of the absence of serum and ultrafiltration is crucial.

Purity Effect on Cell Transcriptome.

In order to evaluate vector transduction effects according to the purity level and independently from any transgene, foreskin fibroblast cells were transduced at M.O.I 40 and 150 with rLV-EF1 (without cDNA) batch B and C derived from the same crude harvest and whose characteristics are summarized in FIG. 15B. Cells were observed 48 hours after transduction as presented in FIG. 15A. A slight growth retardation was visible at M.O.I 40 with batch B transduced cells compared to non-transduced cells, although no growth difference was noticeable after batch C transduction at the same M.O.I. At M.O.I 150, a strong proliferation arrest could be seen with batch B compared to non-transduced cells, whereas only a observed moderate growth retardation was observed with batch C. To explore underlying changes at the transcriptional level, these cells were collected 54 hours post-transduction. RNA was extracted and used to perform Agilent whole human genome microarrays allowing the quantification of nearly all human transcripts. RNA levels from cells transduced with rLV-EF1 batch B and C at M.O.I 40 and 150 were compared to RNA from non-transduced cells. After statistical analyses, probes upregulated or downregulated 1.5-fold or more were retained for each comparison. By intersecting these data, a set of differentially expressed genes with batch B versus non-transduced that were not impacted with batch C versus non-transduced could be identified for each M.O.I. These two sets of genes are represented on scatterplots and profile plots in FIGS. 16A and B for M.O.I 150 and in FIGS. 16C and D for M.O.I 40. As demonstrated, transcript levels variations of selected genes in batch B transduced cells versus non-transduced cells are more pronounced at M.O.I 150 than at M.O.I 40, where variations are slight. These data show a distinct impact on the transcriptome of transduced cells when using different purity levels of vectors.

Serum Effect on Cell Transcriptome.

In order to assess the effects of vector medium composition after production with serum, rLV-EF1 vector (without cDNA) was produced in the presence of 10% serum and concentrated using process B, resulting in a batch B-S, whose characteristics are summarized in FIG. 17B. This batch was used to transduce foreskin cells at M.O.I 40 and M.O.I 150. Cells were observed 48 hours after transduction, as shown in FIG. 17A. A growth arrest is visible after batch B-S transduction compared to non-transduced cells. This growth arrest is stronger at higher M.O.I compared to M.O.I 40. Remarkably, aggregates could be observed after batch B-S transduction, and their volume increases with M.O.I. These cells were collected 54 hours after transduction for RNA extractions and microarray hybridizations. Surprisingly, it was noted, during trypsinization, that cells transduced with batch B-S were more difficult to detach than cells transduced with batch B or C, or non-transduced cells. RNA levels from cells transduced with batch B-S at moderate or higher M.O.I were compared to RNA from non-transduced cells using Agilent whole human genome microarrays. After statistical analyses, probes upregulated or downregulated 1.5-fold or more were retained for each comparison. In order to identify probes associated with vectors produced with serum, we selected probes that were differentially expressed with batch B-S (at M.O.I 40 and 150) versus the non-transduced condition, and that were not affected with batches B and C (at M.O.I 40 and 150). The corresponding set of genes is represented in the profile plot shown in FIG. 18. These data confirm a clear impact of the presence of transduction with a batch produced with serum on the transcriptome of transduced cells on the transcriptome of transduced cells.

Purity Effect on Cell Transcriptome

In order to evaluate vector transduction effects according to the purity level and independently from any transgene, foreskin fibroblast cells were transduced at M.O.I 40 and 150 with viral vector without cDNA (rLV-EF1) batch B and C derived from the same crude harvest. Cells were observed 48 hours after transduction as presented in FIG. 15A. A slight growth retardation was visible at M.O.I 40 with the batch B, although no growth difference was noticeable with batch C at the same M.O.I. At M.O.I 150, a strong proliferation arrest could be seen with batch B, whereas we only observed a moderate growth retardation with batch C. To explore underlying changes at the transcriptional level, these cells were collected 54 hours post-transduction. RNA were extracted and used to perform Agilent whole human genome microarrays allowing the quantification of nearly all human transcripts. RNA levels from cells transduced with viral vector without cDNA (rLV-EF1) batch B and C at M.O.I 150 were compared to RNA from non-transduced cells. After statistical analyses, probes upregulated or downregulated 1.5-fold or more were retained for each comparison. By intersecting these data, a set of differentially expressed genes with batch B that were not affected with batch C could be identified for each M.O.I, as shown in FIGS. 16A-16D (scatterplot M.O.I40 and scatterplot M.O.I150).

Downstream processing of complex macromolecular structures like viruses and vectors is currently one of the main challenges in the field, especially when high M.O.I. are required with resistant cells or using non-integrative lentiviral vectors. In these cases, there are only two possibilities to reach high M.O.I. for a given number of target cells: either the volume of the crude supernatant added to the target cells is increased when it is possible, or the vector supernatant is concentrated. Very often, scientists avoid using high M.O.I.

mainly because they fear the integration of too many vector copy numbers in the target genomic DNA. The effect of contaminants supplied by the producer cells on target cells is not really predictable depending on the target cells. Usually, users attribute the observed toxicity more to the vector itself than to the contaminants present in the vector containing medium.

The applicability of a combination of steps to obtain high quality retroviral and lentiviral vectors was investigated. Suitable operational conditions were initially tested and optimized having as goals the vector recovery and, as well, the product quality in terms of effects on the target cells. Serum free vector production shows a same level of crude production without damaging the titer but leads to some toxicity in the producer cells as shown in FIG. 11. Ultrafiltration was also validated as a good process for concentration and partial purification of retroviral supernatants. As shown, ultrafiltration on central units or ultracentrifugation is an inefficient process not only for crude vector supernatant concentration but also for the concentration of purified vectors after an ultrafiltration or an anion-exchange chromatography step. In fact, to increase the vector titer both batches C and D were submitted to a centrifugation on central units and an increase in the ratio of PP/TU was observed showing that it affects retroviral infectivity probably due to non specific adsorption of the vectors to the membranes. The ultrafiltration process selected here and described as the process C, is based on the concentration of the crude harvest using ultrafiltration technique using hollow fibers. The mode of operation of this technique is by tangential flow filtration using pump forces for pressure set up. Such a technique allows monitoring and controlling the pressure which is an important point for maintaining the vectors integrity and viability. The type of membrane used in this technology does not increase non specific adsorptions compared to the one used for the process B. Surprisingly, it was determined that working pressures, temperature and flow are the key points of a successful process of ultrafiltration. In an embodiment of the invention, he flow comprises between 400 and 600 ml/min and the TMP (transmembrane pressure) is between 6 and 9 psi.

Thus, the concentration and purification of lentiviral vectors for transducing target cells includes a crucial parameter other than the scale-up and the safety: the viability and the cell state following cell transduction. The vector supernatant must be considered as the mix of the vectors themselves and cell contaminants such as host cell proteins and DNA that can induce damaging effects on target cells. Included herein are other parameters to define a vector capable of transducing target cells without affecting cell viability and proliferation:

(i) an average PP/TU ratio between 300 and 900 for a crude batch An increase in this ratio during the concentration step is an indicator of damage to the vector and predicts the existence of vectors debris that could interfere with the transduction and the viability of target cells;

(ii) the DNA removal after concentration at about 82% of initial contaminants and always between 70% and 99% compared to batch A; and (iii) the protein removal after concentration up to 90% of initial contaminants compared to batch A produced in a serum free medium.

Products identified as vectors exhibiting characteristics required for clinical applications (Merten et al., 2010) are different than the products A, C and D based on the use of serum in the culture medium of the producer cells that induces a different composition of the product from the process A. In fact, the composition of proteins and the ratio PP/TU are respectively 25 and 5 fold higher under their conditions before concentration than in batch A. Both parameters have an effect on the downstream concentration/purification processes since final protein concentration is 150 fold higher under their conditions, after concentration, than in our batches C and D. Other analysis of batches dedicated to clinical gene therapy trials have been described in the literature but no link was established between the PP/TU and contaminants contents and their effect on target cells in terms of viability and proliferation.

The products of batches C and D are able to reach high expression efficiency in 100% of transduced cells with less than 30% toxicity at medium M.O.I. and less than 40% at high M.O.I., although product B leads to two fold less cell proliferation than the batch C in the same culture conditions. (FIGS. 13 and 14). The results obtained on cell proliferation with the batch A are equivalent than those obtained with the batch B probably due the large volume required to reach these M.O.I. with a crude batch.

Protein and DNA removal are represented herein by the respective DNA and protein specific activities that ideally are higher than $10^7$ TU/µg of DNA and $10^9$ TU/mg of proteins to prevent a loss of target cell viability or proliferation. Thus, a focus should be made on host cell protein removal. While the B process, corresponding to the obtaining of batch B, allows for only 56% of host protein removal, the C process removes 98% of initial proteins, for example. Thus, even if host cell proteins seem to pass through all membranes, the poor protein removal may be due to non-specific adsorption on the membrane followed by membrane fouling. Such contaminating proteins are then found in the recovery fraction with the vectors.

The results described herein may explain the reluctance of scientists to use high M.O.I. with usual vector batches B due to cell toxicity frequently observed, especially when using primary or stem cells. However, sometimes low or medium M.O.I. are not sufficient to lead to a high level transduction efficiency as it is demonstrated in FIGS. 3A and 3B for hematopoietic stem cells, for example. Early steps of the transduction pathway may be constrained in some target cells leading to low integrated vector copy number and thus require high M.O.I. and an adapted batch C or D.

This toxicity eliminates a sub-population of target cells or inhibits cell differentiation following cell transduction. The present invention shows that these crucial drawbacks can be bypassed in using not only concentrated but also purified vectors. Clearly, ultracentrifugation and centrifugation on ready-to-use units (B batch) are not convenient since they induce damaging effects on targets cells. The use of an ultrafiltration based process (C batch) requires preliminary technical development but allows a high quality batch suitable for cell integrity and proliferation. Moreover, this technique is easily scalable for large scale production. As demonstrate herein, contaminants from the medium do exert an effect on primary delicate cells. This aspect may be considered as well for immortalized cell lines when batch C vectors are used in functional assay for gene target validation or for drug screening. Selected transduced cells resistant to a concentrated but not sufficiently purified vector batch do not represent a normal cell population regarding physiological or metabolic aspects. Another real resulting issue lies in the absence of reproducibility of gene function or drug effect observed in genetically modified immortalized cells and primary models even when the transduction was performed with the same lentiviral tool.

Therefore, the products of the present invention are validated by a ratio between the vector in terms of transducing units and physical particles and the importance of the medium composition that limits the effect on primary and stem cells proliferation and viability, or on the metabolism of such cells, thus allowing reproductive studies of gene function and cell differentiation.

The results according to this invention show the crucial effect of the vector and its medium in target cells for gene therapy, gene target validation both in vitro and in vivo, drug screening or theragnostic and in each field that take into account the cell integrity to explore gene or molecule effect on or a combination of both.

TABLE 1

Performances of related products of this invention obtained with the state of the art concentration process (B) and the processes described in this invention (A, C and D) at a glance

| Process | A | B | C | D |
|---|---|---|---|---|
| Titre (TU/ml) | $1 \times 10^6$ | $1 \times 10^7$–$1 \times 10^8$ | $1 \times 10^7$–$1 \times 10^8$ | $1 \times 10^7$–$1 \times 10^8$ |

TABLE 1-continued

Performances of related products of this invention obtained with the state of the art concentration process (B) and the processes described in this invention (A, C and D) at a glance

| Process | A | B | C | D |
|---|---|---|---|---|
| Process recovery (%) | 100% | 45-55% | 55-70% | 10-20% |
| Concentration factor | N/A | 90-110 | 20-40 | 5-20 |
| Proteins removal (%) | N/A | 55-65% | up to 98% | up to 99.9% |
| DNA removal (%) | N/A | 60-75% | 70-90% | up to 98.8% |
| PP/TU ratio | 200-900 | up to 600 | 200-600 | 100-400 |
| Applications | Immortalized cell lines | Immortalized cell lines | Primary and stem cells | in vivo injection |

TABLE 2

Measures of contaminants and titers in all the batches A, B, C and D

| | Vectalys Batch | A | B | C | D |
|---|---|---|---|---|---|
| | Volume (ml) | 5200 | 1.3 | 171 | 40 |
| Transduction Unit | Titre (TU/ml) | 2.46E+06 | 2.33E+08 | 4.86E+07 | 1.74E+07 |
| | Total TU | 1.3E+10 | 3.0E+08 | 8.3E+09 | 6.9E+08 |
| | Recovery (%) | 100% | 47% | 69% | 6% |
| | Step Yield (%) | 100% | 47% | 69% | 24% |
| Physical particles | Titre p24 (PP/ml) | 7.75E+08 | 1.20E+11 | 1.46E+10 | 4.77E+09 |
| | Total PP | 4.03E+12 | 1.56E+11 | 2.50E+12 | 1.91E+11 |
| | Recovery (%) | 100% | 77% | 65% | 5% |
| Residual DNA | [DNA] (ng/ml) | 589.6 | 33845.33 | 3010.44 | 909.03 |
| | Total DNA (µg) | 3066 | 44 | 515 | 36 |
| | Recovery (%) | 100% | 29% | 18% | 1.25% |
| | Removal Yield (%) | 100% | 71% | 82% | 68% |
| Total Protein | [Protein] (mg/ml) | 0.14 | 12.4 | 0.061 | 0.01 |
| | Total Protein (mg) | 728 | 16.1 | 10.4 | 0.4 |
| | Recovery (%) | 100% | 44% | 2.1% | 0.08% |
| | Removal Yield (%) | 100% | 56% | 98% | 97% |
| Specific activity | TU/µg DNA | 4.17E+06 | 6.88E+06 | 1.61E+07 | 1.91E+07 |
| | TU/mg Protein | 1.76E+07 | 1.88E+07 | 7.96E+08 | 3.47E+09 |
| | PP/TU | 5.70E+00 | 5.33E+00 | 1.26E−01 | 2.88E−02 |
| | | 315 | 515 | 301 | 275 |
| Purification Level | TU/DNA | 1 | 1.7 | 3.9 | 4.6 |
| | TU/Protein | 1 | 1.1 | 32.4 | 141 |
| | PP/TU | 1 | 1.6 | 1 | 0.9 |

TABLE 3

Impact of the crude vector composition obtained from different harvests times, with or without sodium butyrate induction on transfected cells.

| | Harvests times after transfection(H) | 40 | 48 | 64 | 72 | 96 | 40 | 48 | 64 | 72 |
|---|---|---|---|---|---|---|---|---|---|---|
| | Harvests times after medium removal (H) | 16 | 24 | 40 | 48 | 64 | 16 | 24 | 40 | 48 |
| | Production time/harvest (H) | 16 | 8 | 16 | 8 | 16 | 16 | 8 | 16 | 8 |
| | Conditions | Without sodium butyrate induction | | | | | With sodium butyrate induction | | | |
| | Harvest | R1-32 h | R2-48 h | R3-56 h | R4-72 h | R5-96 h | R1-32 h | R2-48 h | R3-56 h | R4-72 h |
| | Volume (ml) | 7.5 | 7.5 | 7.5 | 7.5 | 7.5 | 7.5 | 7.5 | 7.5 | 7.5 |
| Transduction Unit | Titre (TU/ml) | 1.40E+07 | 8.80E+06 | 8.80E+06 | 3.30E+06 | 3.60E+06 | 2.30E+07 | 3.50E+06 | 4.50E+06 | 2.30E+06 |
| | TU/Production | | | 2.69E+08 | | | | | 2.71E+08 | |
| Total DNA | [DNA] (µg/ml) | 0.43 | 0.57 | 1.36 | 1.12 | 1.74 | 3.819 | 3.364 | 3.878 | 2.155 |
| | DNA average | | | 1.05 | | | | | 3.07 | |
| LDH | % Cytotoxicity | 7.8% | 6.7% | 25.4% | 16.4% | NA | 40.7% | 18.3% | 41.8% | 22.2% |
| Specific activity | TU/µg DNA | 3.28E+07 | 1.53E+07 | 6.45E+06 | 2.94E+06 | 5.53E+05 | 6.02E+06 | 1.04E+06 | 1.16E+06 | 1.07E+06 |
| | PP/TU | 119 | 40 | 100 | 63 | 48 | 118 | 77 | 102 | 43 |

TABLE 3-continued

Impact of the crude vector composition obtained from different harvests times, with or without sodium butyrate induction on transfected cells.

| | | | | | | | |
|---|---|---|---|---|---|---|---|
| | | Harvests times after transfection(H) | 96 | 64 | 88 | 64 | 88 |
| | | Harvests times after medium removal (H) | 64 | 40 | 64 | 40 | 64 |
| | | Production time/harvest (H) | 16 | 40 | 24 | 40 | 24 |
| | | Conditions | With sodium butyrate induction | Without sodium butyrate induction | | Without sodium butyrate induction | |
| | | Harvest | R5-96 h | R1-64 h | R2-88 h | R1-64 h | R2-88 h |
| | | Volume (ml) | 7.5 | 7.5 | 7.5 | 7.5 | 7.5 |
| Transduction Unit | | Titre (TU/ml) | 2.80E+06 | 1.10E+07 | 3.60E+06 | 1.50E+07 | 3.30E+06 |
| | | TU/Production | 2.71E+08 | 1.10E+08 | | 1.37E+08 | |
| Total DNA | | [DNA] (µg/ml) | 2.127 | 2.44 | 3.36 | 9.03 | 5.39 |
| | | DNA average | 3.07 | 2.90 | | 7.21 | |
| LDH | | % Cytotoxicity | NA | 81.9% | 48.4% | 97.4% | 52.4% |
| Specific activity | | TU/µg DNA | 1.32E+06 | 4.51E+06 | 1.07E+06 | 1.66E+06 | 6.12E+05 |
| | | PP/TU | 40,3571429 | 262 | 141 | 90 | 187 |

REFERENCES

Aloia R C, Tian H, Jensen F C. 1993. Lipid composition and fluidity of the human immunodeficiency virus envelope and host cell plasma membranes. Proc Natl Acad Sci USA 90 (11):5181-5.

Andreadis S T, Roth C M, Le Doux J M, Morgan J R, Yarmush M L. 1999. Large-scale processing of recombinant retroviruses for gene therapy. Biotechnol Prog 15(1): 1-11.

Baekelandt V, Eggermont K, Michiels M, Nuttin B, Debyser Z. Optimized lentiviral vector production and purification procedure prevents immune response after transduction of mouse brain. Gene Ther. November 2003; 10(23):1933-40.

Brunner D, Frank J, Appl H, Schöffl H, Pfaller W, Gstraunthaler G. Serum-free cell culture: the serum-free media interactive online database. ALTEX. 2010; 27(1):53-62.

Coffin J M, Hughes S H, Varmus H E (eds). Retroviruses. Cold Spring Harbor Laboratory Press, 1997.

Clapham P, Nagy K and Weiss R A (1984). Pseudotypes of human T-cell leukemia virus types 1 and 2: neutralization by patients' sera. Proc Natl Acad Sci USA 81, 2886-2889.

Coroadinha A S, Ribeiro J, Roldao A, Cruz P E, Alves P M, Merten O W, Carrondo M J. 2006. Effect of medium sugar source on the production of retroviral vectors for gene therapy. Biotechnol Bioeng 94(2):24-36.

Cooper A R, Patel S, Shantha Senadheeraa S, Plath K, Kohn D B, Hollisa R P. Highly efficient large-scale lentiviral vector concentration by tandem tangential flow filtration. Journal of Virological Methods, Volume 177, Issue 1, October 2011, 1-9.

Grzenia D L, Carlson J O, Wickramasinghe. Tangential flow filtration for virus purification. J. Membrane Science, 321 (2008) 373-380.

Le Doux J M, Davis H E, Morgan J R, Yarmush M L 1999. Kinetics of retrovirus production and decay. Biotech. Bioeng. 63, 654-662.

Manganini M, Serafini M, Bambacioni F, Casati C, Erba E (2002). A human immunodeficiency virus type 1 pol gene-derived sequence (cPPT/CTS) increases the efficiency of transduction of human nondividing monocytes and T lymphocytes by lentiviral vectors. Hum Gene Ther 13: 1793-1807.

Merten O W, Charrier S, Laroudie N, Fauchille S, Dugué C, Jenny C, Audit M, Zanta-Boussif M A, Chautard H, Radrizzani M, Vallanti G, Naldini L, Noguiez-Hellin P, Galy A. Large-scale manufacture and characterization of a lentiviral vector produced for clinical ex vivo gene therapy application. Hum Gene Ther. March 2011; 22(3): 343-56.

Miguel Sena-esteves, Jessica Tebbets, Sabine Steffens, Timothy Crombleholme, Alan W. Flake. Optimized large-scale production of high titer lentivirus vector pseudotypes. Journal of Virological Methods 122 (2004) 131-139.

O'Keeffee R S, Johnston M D, Slater N K. 1999. The affinity adsorptive recovery of an infectious herpes simplex virus vaccine. Biotechnol Bioeng 62(5):537-45.

Ott D E. 1997. Cellular proteins in HIV virions. Rev Med Virol 7(3):167-80.

Reiser, J. Production and concentration of pseudotyped HIV-1 based gene transfer vectors. Gene Ther 7: 910-913.

RimaiL, Salmee I, Hart D, Liebes L, Rich M A, McCormick J J. 1975. Electrophoretic mobilities of RNA tumor viruses. Studies by Doppler-shifted light scattering spectroscopy. Biochemistry 14(21):4621-7.

Rodrigues T, Carvalho A, Carmo M, Carrondo M J T, Alves P M, Cruz P E. Scaleable purification process for gene therapy retroviral vectors. J. Gene Medicine, 9 (2007) 233-243.

Rodrigues T, Carrondo M J T, Alves P M, Cruz P E. 2007. Purification of retroviral vectors for clinical application: Biological implications and technological challenges. J Biotechnol 127(3): 520-41.

Salmeen I, Rimai L, Liebes L, Rich M A, McCormick J J. 1975. Hydrodynamic diameters of RNA tumor viruses. Studies by laser beat frequency light scattering spectroscopy of avian myeloblastosis and Rauscher murine leukemia viruses. Biochemistry 14(1):134-41.

Selvaggi T A, Walker R E, Fleisher T A. Development of antibodies to fetal calf serum with arthus-like reactions in human immunodeficiency virus-infected patients given syngeneic lymphocyte infusions. Blood. Feb. 1, 1997; 89(3):776-9.

Slepushkin V, Chang N, Cohen R, Gan Y, Jiang B, Deausen E, Berlinger D, Binder G, Andre C, Humeau L, Dropulic B. Large scale purification of a lentiviral vector by size exclusion chromatography or mustang Q ion exchange capsule. Bioprocessing Journal September/October (2003) 89-95.

Sven Ansorge, Olivier Henry, Amine Kamen. Recent progress in lentiviral vector mass production. Biochemical Engineering Journal 48 (2010) 362-377.

Trubey C M, Chertova E, Coren L V, Hilburn J M, Hixson C V, Nagashima K, Lifson J D, ott D E. 2003. Quantification of HLA class II protein incorporated into human immunodeficiency type 1 virions purified by anti CD-45 immunoaffinity depletion of microvesicles. J Virol 77(23):12699-709.

Trubey C M, Chertova E, Coren L V, Hilburn J M, Hixson C V, Nagashima K, Lifson J D, ott D E. 2003. Quantification of HLA class II protein incorporated into human immunodeficiency type 1 virions purified by anti CD-45 immunoaffinity depletion of microvesicles. J Virol 77(23):12699-709.

Van Reis R, Zydney A. Membrane separations in biotechnology. Curr Opin Biotechnol. April 2001; 12(2):208-11.

Verhoeyen E, Cosset F L. 2004. Surface-engineering of lentiviral vectors. J Gene Med 6 Suppl 1:S83-94.

Yee J K, Friedmann T, Burns J C. 1994. Generation of high-titer pseudotyped retroviral vectors with very broad host range. Methods Cell Biol 43 Pt A: 99-112.

Yamada K, McCarty D M, Madden V J, Walsh C E. Lentivirus vector purification using anion exchange HPLC leads to improved gene transfer. Biotechniques. May 2003; 34(5):1074-8, 1080.

Zufferey R, Donello J E, Trono D, Hope T J (1999) Woodchuck hepatitis virus post transcriptional regulatory element enhances expression of transgenes delivered by retroviral vectors. J. Virol 73: 2886-2892.

What is claimed:

1. A method for producing a purified RNA based viral vector composition, said method comprising:
   (i) culturing a viral vector transfected producer cell in serum-free medium, said producer cell modified to complement deletions in the viral genome upon which the viral vector is based, under suitable conditions to permit the production of viral vector particles;
   (ii) collecting the supernatant containing said viral vector particles at multiple times up to 72 hours post-transfection, wherein the first collection occurs between 24 and 36 hours post-transfection;
   (iii) determining the ratio of total physical particles/transducing units (PP/TU) for each of the supernatants collected in (ii), wherein the PP/TU ratio of each of the collected supernatants is measured to be from 900:1 to 200:1;
   (iv) pooling said collected supernatants; and
   (v) subjecting said pooled supernatants to tangential ultrafiltration and/or diafiltration,
   wherein the ratio of total physical particles/transducing units (PP/TU) in the RNA based viral vector composition is no greater than the PP/TU of any of the collected supernatants of (ii).

2. The method of claim 1, further comprising a step of ion-exchange chromatography.

3. The method of claim 1, wherein the ultrafiltration is operated on polysulfone hollow-fiber cartridges.

4. The method of claim 1, wherein the retentate obtained following tangential ultrafiltration and/or diafiltration is treated with a nuclease.

5. The method of claim 4, wherein the nuclease is benzonase or a DNase.

6. The method of claim 2, resulting in a preparation of purified RNA based viral vector particles wherein the removal of DNA contaminants is at least 98% of such contaminants present in the initial serum-free culture medium, and the removal of cellular proteins contaminants is at least 99% of the cellular proteins contained in the initial serum-free culture medium.

7. The method of claim 1, resulting in a preparation of purified RNA based viral vector particles, wherein the removal of DNA contaminants is less than 80% up to 90% of the content of such contaminants present in the initial serum-free culture medium, and the removal of cellular proteins contaminants up to 98% of the content of such contaminants present in the initial serum-free culture medium.

8. A purified RNA based viral vector composition produced using the method of claim 1 wherein the RNA based viral vector composition is one wherein the ratio of total physical particles/transducing units (PP/TU) is between 200:1 up to 600:1.

9. A purified RNA based viral vector composition produced using the method of claim 2 wherein the RNA based viral vector composition is one wherein the ratio of total physical particles/transducing units (PP/TU) is between 100:1 up to 400:1.

10. The method of claim 1, wherein the multiple collections are conducted at 8-16 hour intervals.

11. The purified RNA based viral vector composition of claim 8 having a specific activity of greater than $1.88 \times 10^7$ TU/mg protein and greater than $6.88 \times 10^6$ TU/μg DNA.

12. The purified RNA based viral vector composition of claim 9 having a specific activity of greater than $7.96 \times 10^8$ TU/mg protein and greater than $1.61 \times 10^7$ TU/μg DNA.

* * * * *